(12) United States Patent
Kobayashi

(10) Patent No.: US 7,717,709 B2
(45) Date of Patent: May 18, 2010

(54) CONTACT CAP FOR DENTAL TOOTH MEASURING APPARATUS AND MEASURING METHOD USING DENTAL TOOTH MEASURING APPARATUS

(75) Inventor: Hiroyoshi Kobayashi, Hachioji (JP)

(73) Assignee: Olympus Corporation, Tokyo (JP)

( * ) Notice: Subject to any disclaimer, the term of this patent is extended or adjusted under 35 U.S.C. 154(b) by 121 days.

(21) Appl. No.: 11/639,115

(22) Filed: Dec. 14, 2006

(65) Prior Publication Data
US 2007/0141528 A1  Jun. 21, 2007

(30) Foreign Application Priority Data
Dec. 19, 2005 (JP) .............................. 2005-365460

(51) Int. Cl.
*A61C 1/00* (2006.01)
*A61C 3/00* (2006.01)
(52) U.S. Cl. ........................................................ 433/29
(58) Field of Classification Search ................... 433/26, 433/29, 72, 214, 31, 140; 229/26, 29, 72, 229/214; 604/77; 128/201.26
See application file for complete search history.

(56) References Cited

U.S. PATENT DOCUMENTS

| | | | |
|---|---|---|---|
| 5,048,519 A | * | 9/1991 | Kasama et al. ......... 128/207.14 |
| 6,964,567 B2 | * | 11/2005 | Kerschbaumer et al. ....... 433/26 |
| 2006/0110700 A1 | * | 5/2006 | Cipolla et al. ................. 433/29 |

FOREIGN PATENT DOCUMENTS

| | | |
|---|---|---|
| JP | 2002-355263 A | 12/2002 |
| JP | 2004-305429 A | 11/2004 |

* cited by examiner

*Primary Examiner*—Cris L Rodriguez
*Assistant Examiner*—Matthew M Nelson
(74) *Attorney, Agent, or Firm*—Frishauf, Holtz, Goodman & Chick, P.C.

(57) ABSTRACT

A contact cap is attached to a top cover of a camera of a dental tooth measuring apparatus, and when shooting, positioning of the tooth to be measured is performed with a bite section being slightly bitten by both of adjacent teeth sandwiching the tooth to be measured, and with keeping a state where the inside of the adjacent teeth is in contact with a camera side surface of a positioning convex section. Positioning of the tooth to be measured and the adjacent teeth with variation among individuals with respect to the camera can be performed more precisely.

16 Claims, 17 Drawing Sheets

FIG. 20
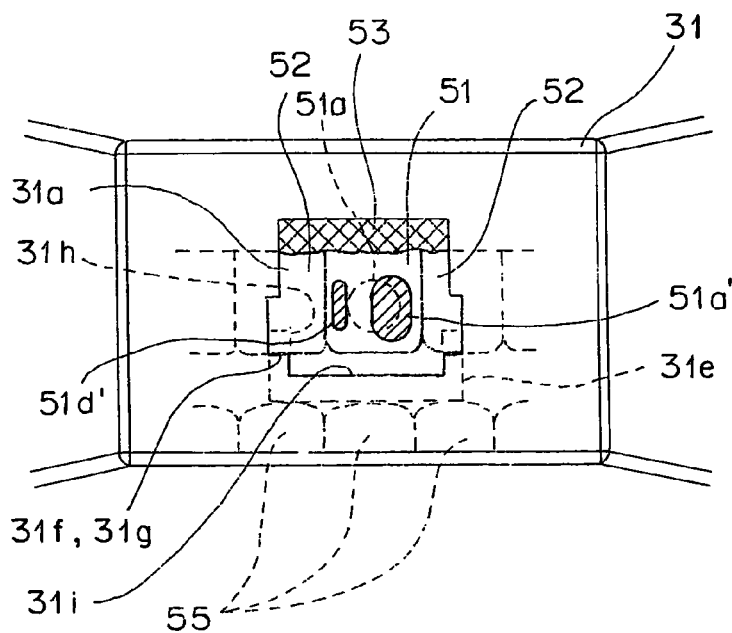
FIG. 21 (CCD side)
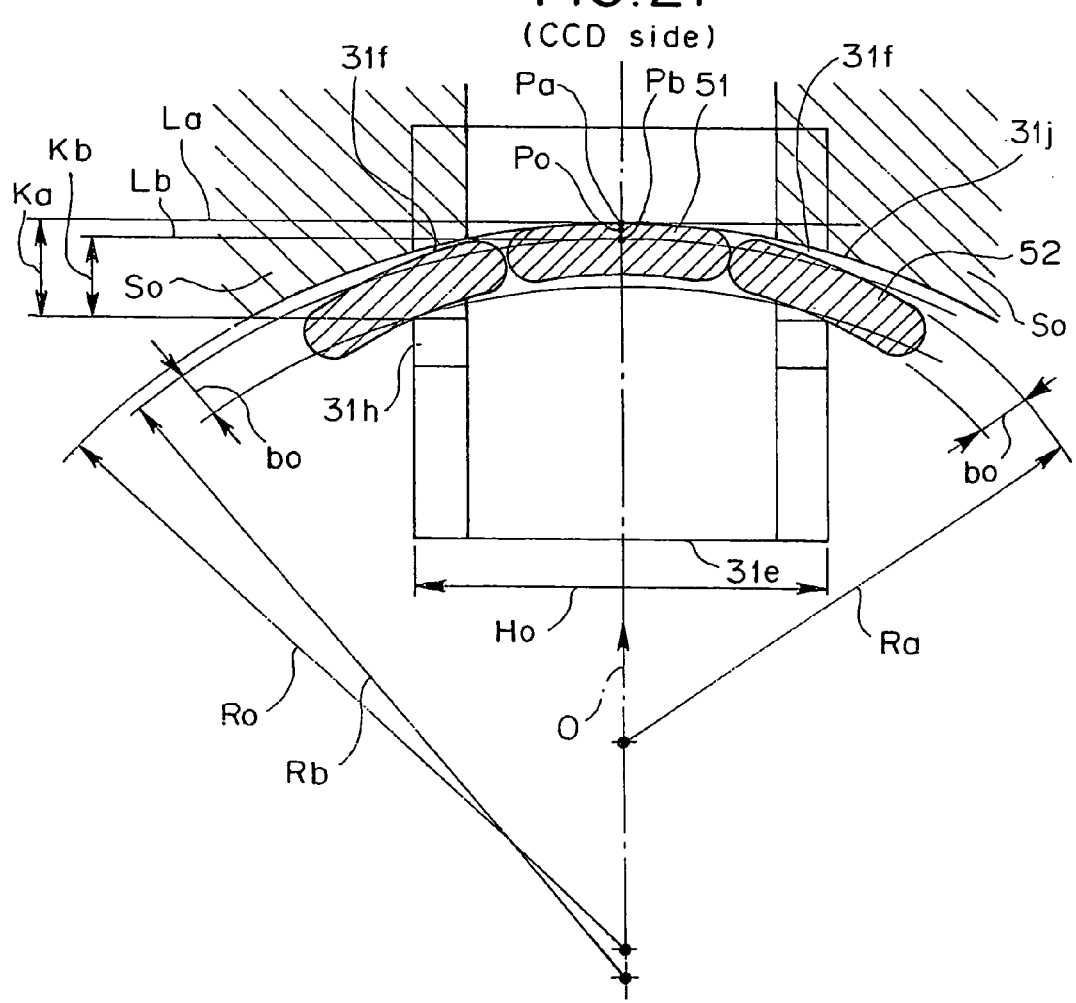

CONTACT CAP FOR DENTAL TOOTH MEASURING APPARATUS AND MEASURING METHOD USING DENTAL TOOTH MEASURING APPARATUS

CROSS REFERENCE TO RELATED APPLICATION

This application claims benefit of Japanese Application No. 2005-365460 filed in Japan on Dec. 19, 2005, the contents of which are incorporated by this reference.

BACKGROUND OF THE INVENTION

1. Field of the Invention

The present invention relates to a contact cap for a dental tooth measuring apparatus as an ancillary apparatus for shooting applied at shooting (measuring) in the dental tooth measuring apparatus and a measuring method using the dental tooth measuring apparatus.

2. Description of the Related Art

When treatment with an artificial tooth (implant) is given to a patient at a dental clinic, especially an artificial tooth for an incisor is put, the colors of the patient's vital teeth (or non-vital teeth) to be adjacent to the incisor need to be measured by some method and compared for selecting an artificial tooth with suitable color for the teeth. As a method for measuring a shade of a tooth at present, the patient's teeth are compared with reference plates called a shade guide, and decide the number of the shade guide which is visually determined as the nearest shade by the dentist as the shade of the tooth. With the number, bleaching effect is checked or the number is notified to a dental technician's office to make an artificial tooth (implant).

In the conventional method of deciding a shade of an artificial tooth by visually determining with the abovementioned shade guide, the determination is susceptible to lighting and even the same tooth of the same patient may be determined as a different shade depending on the type of lighting in the room or influence of an outside light. The determination may also largely diversify according to the physical condition of the dentist (or the dental technician) that performs the determination so that it is difficult to satisfactorily select an artificial tooth.

What needed is a dental tooth measuring apparatus (shooting apparatus) which can shoot a corresponding tooth needed for correctly acquiring a shade of the tooth without being affected by lighting or a determiner under such circumstances and can acquire correct shade information of the tooth by the image information. As for the dental tooth measuring apparatus (shooting apparatus), a dental camera of the Patent Document 1 or a buccal cavity shooting apparatus of the Patent Document 2 are disclosed.

For the dental camera disclosed in the Japanese Patent Laid-Open No. 2002-355263 (hereinafter referred to as Patent Document 1), a mouthpiece is used as a hood to be attached to an opening for shooting. The mouthpiece has an engaging protrusion section and wing section, which position a tooth to be measured.

The buccal cavity shooting apparatus in the Japanese Patent Laid-Open No. 2004-305429 (hereinafter referred to as Patent Document 2) is for shooting a buccal cavity by applying a bitten mouthpiece to a light shielding cover attached to the apparatus.

When shooting is actually performed by the abovementioned tooth measuring apparatus, a single tooth (vital tooth) needs to be closely shot. If shooting is merely performed in a conventional closely shooting state, it is inevitably affected by lighting. Then, shooting needs to be performed under lighting of special light. In such a case, an outside light needs to be shielded and a contact cap for shooting which makes a hood for positioning an objective tooth more close to a shooting position needs to be attached to a camera. Fine adjustment needs to be made to the angle of gradient of the tooth to be measured, as the surface of a part to be measured is not necessarily kept in an upright position to the optical axis for shooting in a positioned state at shooting.

SUMMARY OF THE INVENTION

The contact cap for a dental tooth measuring apparatus according to the present invention includes a cap section which is attachable to cover a periphery of a shooting window section of the tooth measuring apparatus, an opening section which has a size to include a tooth to be measured and parts of a pair of adjacent teeth adjacent to the tooth to be measured, wherein the opening section is arranged before the cap section and faces the shooting window section when the cap section is attached to the tooth measuring apparatus, and a protrusion section which is placed below the opening section so as to protrude ahead of the tooth measuring apparatus and which is biteable by the pair of adjacent teeth. A pair of pillar convex sections are formed on an upper portion of the protrusion section for positioning tongue sides of the pair of adjacent teeth, wherein the pair of pillar convex sections are arranged separately from each other, and a wall section is provided on the cap section and is placed with a predetermined gap at a side of the tooth measuring apparatus with respect to the pair of pillar convex sections.

The measuring method with the dental tooth measuring apparatus according to the present invention is a measuring method for measuring the tooth to be measured by the dental tooth measuring apparatus attached with a contact cap, wherein the method includes inserting the contact cap into a buccal cavity of a patient. The contact cap includes: (i) a cap section which is attachable to cover a periphery of a shooting window section of the dental tooth measuring apparatus, (ii) an opening section which is arranged before the cap section and which faces the shooting window section when the cap section is attached to the tooth measuring apparatus, and (iii) a protrusion section which is placed below the opening section so as to protrude ahead of the dental tooth measuring apparatus and which is biteable by a pair of adjacent teeth adjacent to the tooth to be measured, (iv) a pair of pillar convex sections formed on an upper portion of the protrusion section for positioning tongue sides of the pair of adjacent teeth, wherein the pair of pillar convex sections are arranged separately from each other, and (v) a wall section which is provided on the cap section and which is placed with a predetermined gap at a side of the tooth measuring apparatus with respect to the pair of pillar convex sections. The method performs the measuring by adjusting a relative angle between the dental tooth measuring apparatus and the tooth to be measured while observing the position of a regular reflection region of the tooth to be measured appearing in an image shot by the dental tooth measuring apparatus.

The other features and advantages of the present invention will be apparent from the description below.

BRIEF DESCRIPTION OF THE DRAWINGS

FIG. 20 is a diagram showing a shooting state when the tooth to be measured shown in a view seen from the E arrow of FIG. 17;

FIG. 21 is a plan arrangement view showing a range of a wall section arrangement place against a curvature radius and a bite width of a row of teeth in the contact cap of FIG. 10;

DETAILED DESCRIPTION OF THE PREFERRED EMBODIMENTS

Embodiments of the present invention will be described with reference to the drawings.

Figure 1:
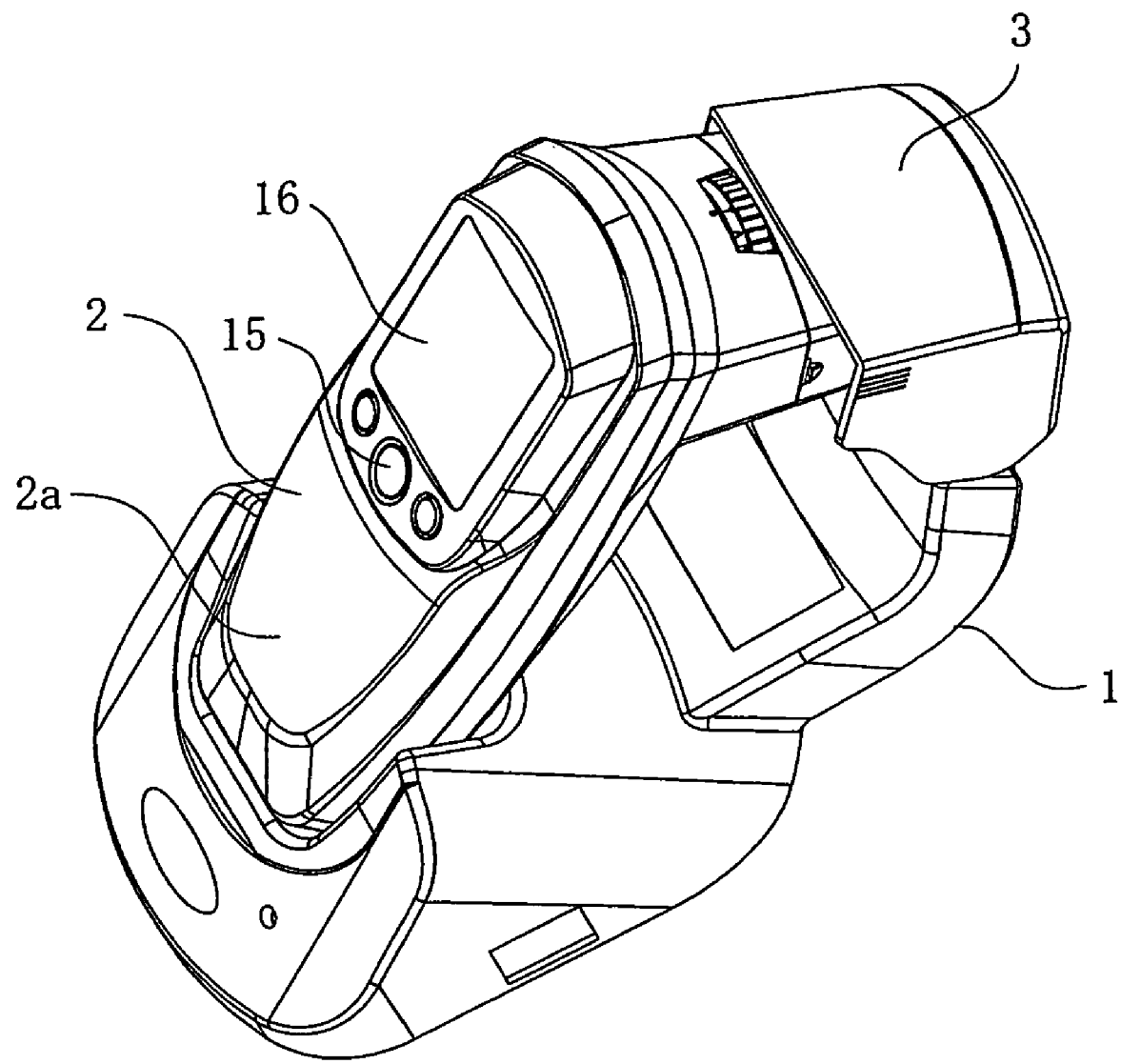
FIG. 1 is an oblique perspective diagram showing an appearance of an HMSC apparatus, which is a dental tooth measuring (shooting) apparatus including a camera and a cradle, to which a contact cap for dental tooth measuring of an embodiment of the present invention can be applied.
Figure 2:
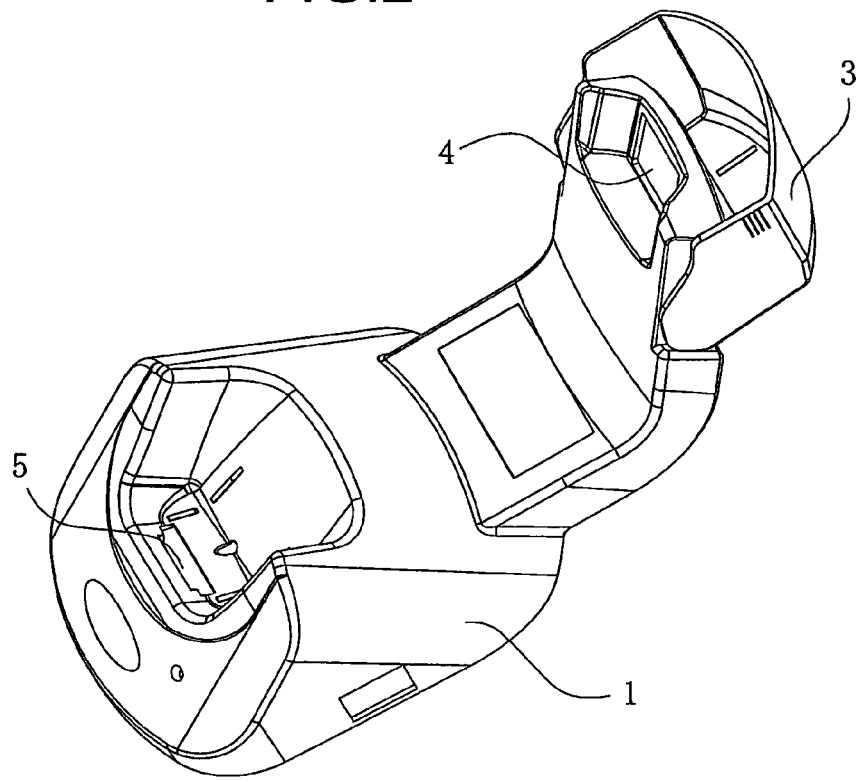
FIG. 2 is an oblique perspective diagram showing the cradle of the HMSC apparatus of FIG. 1 and shows a state of light shielding cover being opened.
Figure 3:
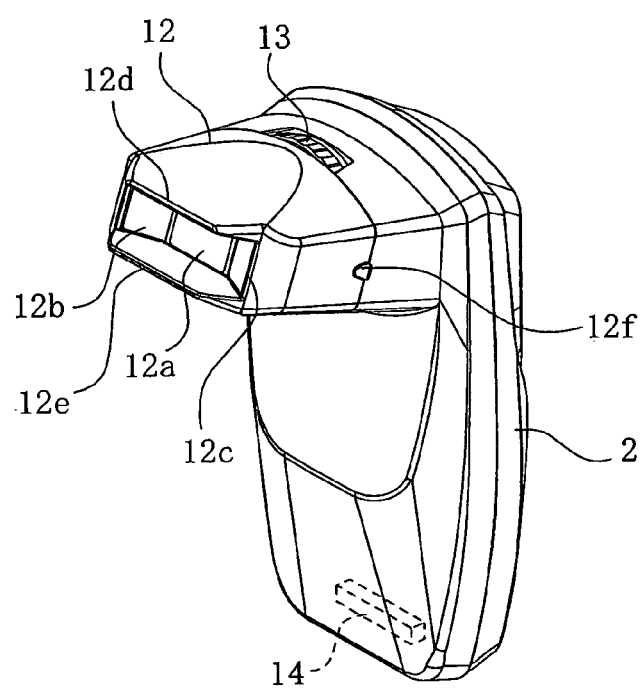
FIG. 3 is an oblique perspective diagram seen from a front side showing an appearance of the camera of the HMSC apparatus of FIG. 1.
Figure 4:
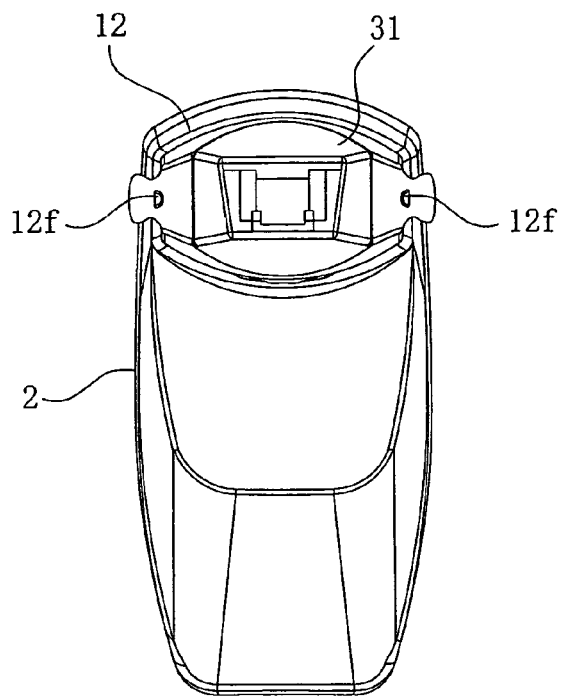
FIG. 4 is a front view showing the contact cap of FIG. 1 is attached on the camera of FIG. 3.
Figure 5:
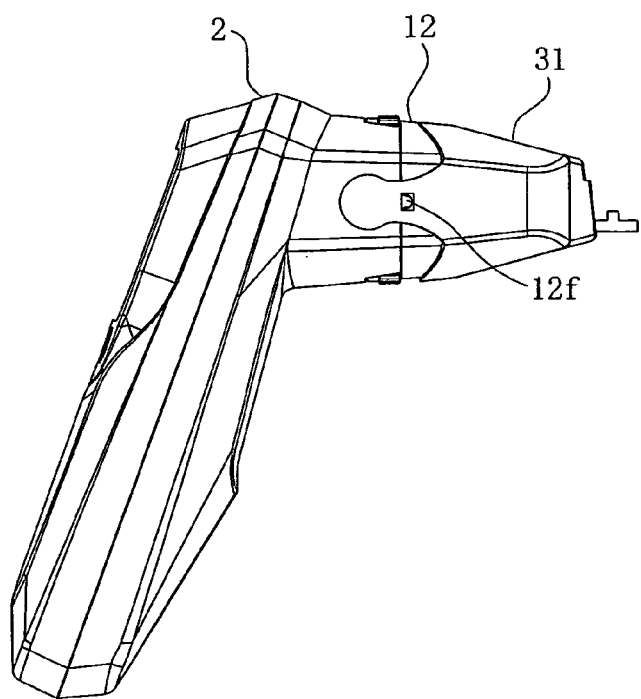
FIG. 5 is a side view showing the contact cap is attached to the camera of FIG. 3.

FIG. 1 is an oblique perspective diagram showing an appearance of the HMSC apparatus (Handy Multi-Spectral Camera), which is a dental tooth measuring (shooting) apparatus including a camera and a cradle, to which a contact cap for dental tooth measuring of an embodiment of the present invention can be applied, showing a state that measuring is performed where the camera is attached to the cradle with a light shielding cover closed. FIG. 2 is an oblique perspective diagram showing the cradle and shows a state of light shielding cover being opened. FIG. 3 is an oblique perspective diagram showing an appearance of the camera. FIG. 4 is a front view showing the camera with the contact cap being attached. FIG. 5 is a side view of the camera with the contact cap being attached to.

Figure 6:
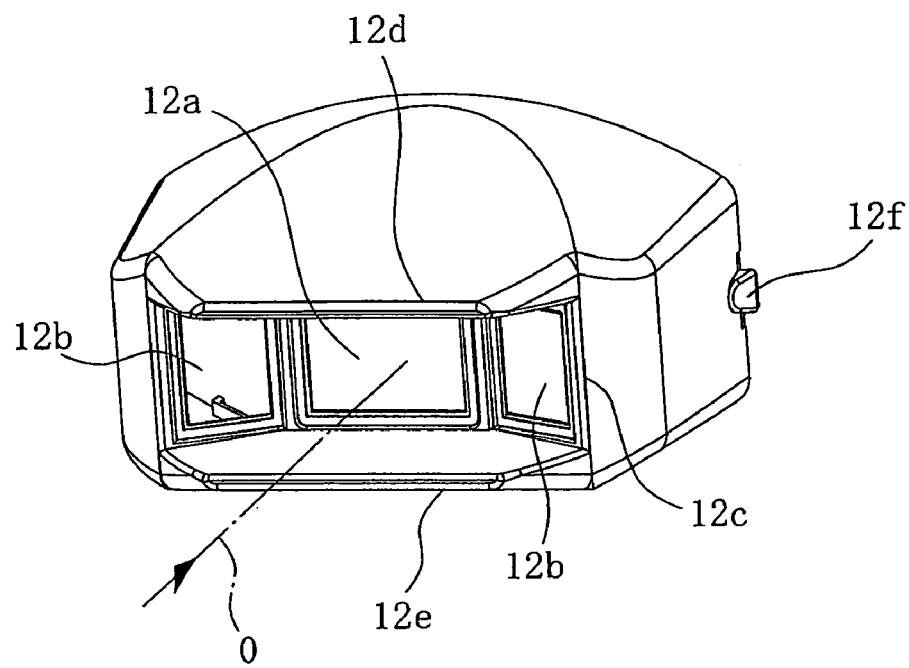
FIG. 6 is an oblique perspective diagram of a top cover of the camera of FIG. 3.
Figure 7:
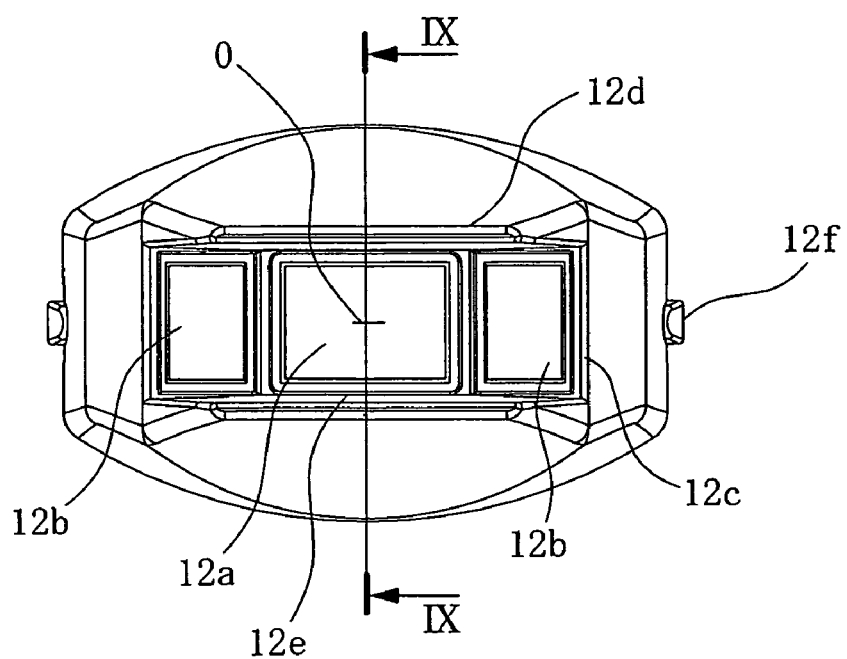
FIG. 7 is a front view of the top cover of FIG. 6.
Figure 8:
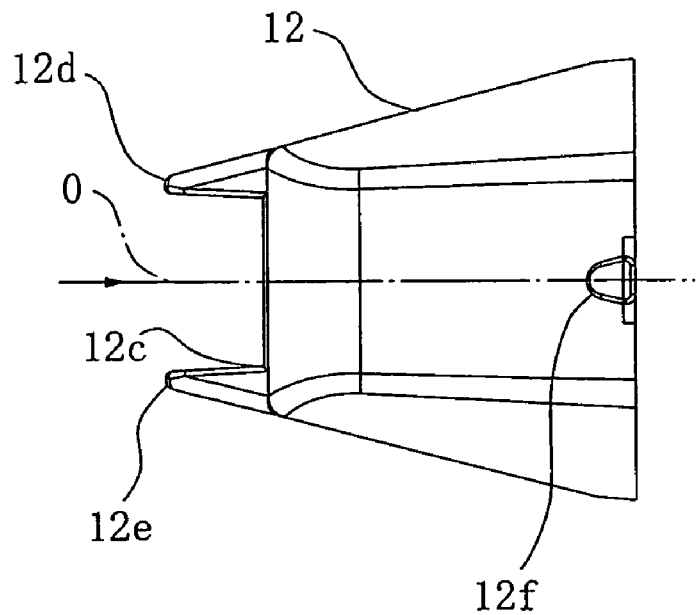
FIG. 8 is a side view showing the top cover of FIG. 6.
Figure 9:
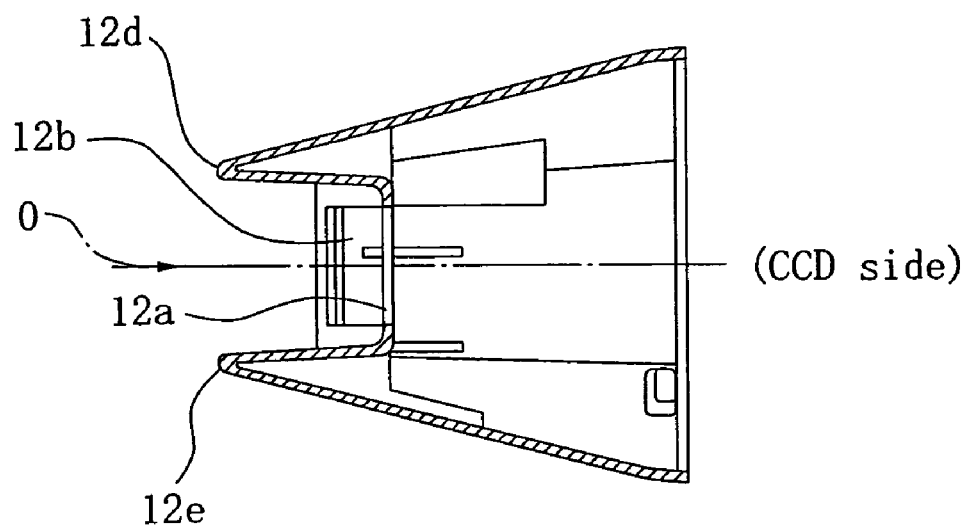
FIG. 9 is an IX-IX cross sectional diagram of FIG. 7.

FIGS. 6 to 9 are diagrams showing appearances, cross-sectional shapes of the top cover to be fixed on the front of the camera: FIG. 6 is an oblique perspective diagram of the top cover. FIG. 7 is a front view of the top cover. FIG. 8 is a side view of the top cover. FIG. 9 is an IX-IX cross sectional diagram of FIG. 7.

The HMSC apparatus includes a cradle 1 and a camera 2 which can be removed from the cradle 1 as shown in FIGS. 1 to 3.

The cradle 1 charges an internal battery of the camera 2 with the camera 2 being attached thereto and transfers shot image data captured in the camera 2 via a USB to a personal computer (not shown). A reference plate for shot image data calibration 4 (FIG. 2) of the camera 2 is built in the cradle 1 with a light shielding cover 3 which can be rotated for shielding a light around the reference plate 4 when the camera 2 is attached thereto is attached to.

The camera 2 includes an LED illumination system 17 including a plurality of LEDs in the camera body 2a, a shooting optical system 18 which can focus with shooting optical axis O (hereinafter, described as an optical axis O), an image capturing section 19 (described in FIG. 17 later) including a color CCD, an LCD display section 16, an image processing section, an image memory section, a communication controlling section (not shown), and a connector for connecting 14 (FIG. 3). To the front of the camera body 2a, the top cover 12 is firmly fixed.

In the description below, the front of the camera 2 and the contact cap for dental tooth measuring apparatus 31 to be described later is the object side in the direction of the optical axis O (side of a tooth to be measured) and the back of them is the CCD side of the image capturing section (side of a camera).

On the top cover 12, a shooting window section 12a is placed in the center of the front with an illumination window section 12b on both sides as shown in FIGS. 6 to 9, with a notch section 12c having top sections 12d, 12e being provided. On both ends at the back, a latching protrusion 12f for latching the contact cap for the dental tooth measuring apparatus (hereinafter, described as a contact cap) 31 is arranged.

Figure 17:
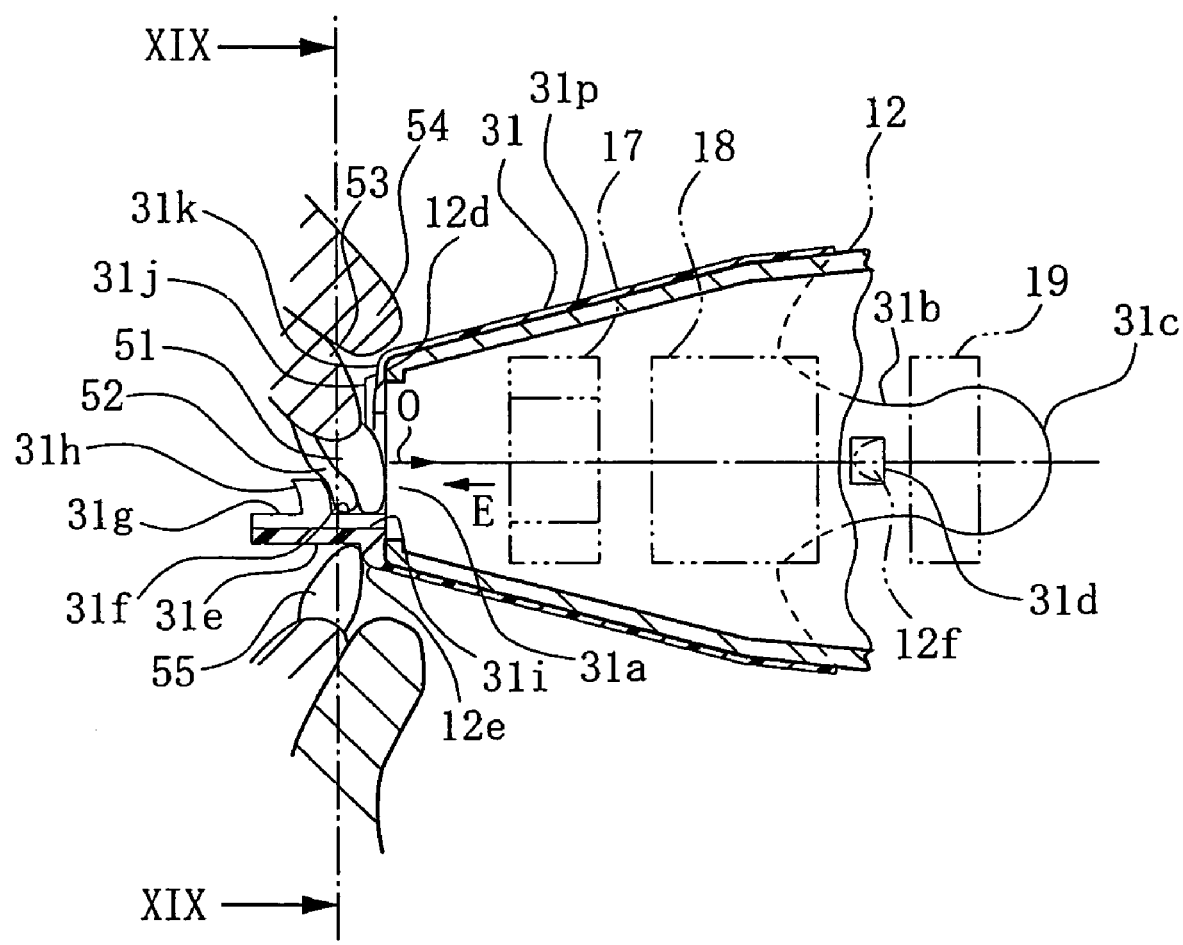
FIG. 17 is a diagram showing a case where a tooth to be measured is being shot with the camera of FIG. 3 by a XV-XV cross sectional diagram.

The LED illumination system 17, the shooting optical system 18, and the image capturing section 19 are provided in a prescribed arrangement along the optical axis O in the camera body 2a at the back of the shooting window section 12a at the front of the top cover 12 (FIG. 17).

On the exterior of the top cover 12, a contact cap 31 (described later by FIG. 10 and the like) for positioning the tooth to be measured during a measurement shooting mode is attached as shown in FIGS. 4 and 5.

The notch section 12c arranged in front of the top cover 12 is provided for convenience of cleaning dirt on the shooting window section 12a.

In the HMSC apparatus, the camera 2 is attached to the cradle 1 and charged, an image of the reference plate 4 is captured, and calibration on the shot image data is performed. After the calibration, the camera 2 is detached from the cradle 1 and shooting is performed in three shooting modes to be described later. During the shooting, a person who shoots holds the body of the camera 2 with a hand, focuses on the object by observing the object image on the LCD display section 16 and turning a focus ring 13, and captures an image of the object (the patient's face, the entire jaw) by operating an operating switch button 15. When a single tooth of the teeth to be measured is shot, the tooth is shot with the focus ring 13 being moved to a predetermined turning position set in advance.

The three shooting modes are a countenance shooting mode, an entire jaw shooting mode, a measurement shooting mode. In the countenance shooting mode, the entire face of the patient is shot by a color CCD under the outside light and referential image data (RGB shot image data) is captured.

In the entire jaw shooting mode, the entire teeth of the patient are shot by a color CCD also under the outside light and referential image data (RGB shot image data) is captured.

In the measurement shooting mode, a contact cap 31 to be described later is attached to the top cover 12 (FIG. 4) of the tip of the camera 2 to shield the outside light and stably position a single tooth of the teeth to be measured to the shooting opening. Then, multi-band shooting is performed on a single tooth of a patient's specified tooth to be measured (vital teeth) (may be two teeth) through an opening section of the attached contact cap 31 with an illumination by a plurality of LEDs with a plurality of wavelengths. With this shooting, multi-band shooting image data for correctly measuring the single teeth's shade is captured.

When shooting ends in each of the abovementioned shooting modes, the camera 2 is attached to the cradle 1 again, and each of the shot image data is transferred to the personal computer via the USB. In the personal computer, filing of RGB shot image data, calibration correction of multi-band shot image data, color degree calculation of multi-band shot image data, and shade guide number determination are performed. Then, shade guide and color degree data is stored in association with the RGB shot image data. The stored data is sent to a dental technician's office and materials for the artificial tooth to match the shot vital tooth is selected.

A shape of the contact cap 31 to be attached to the top cover 12 of the camera 2 during the shooting in the abovementioned measurement shooting mode will be described.

Figure 10:
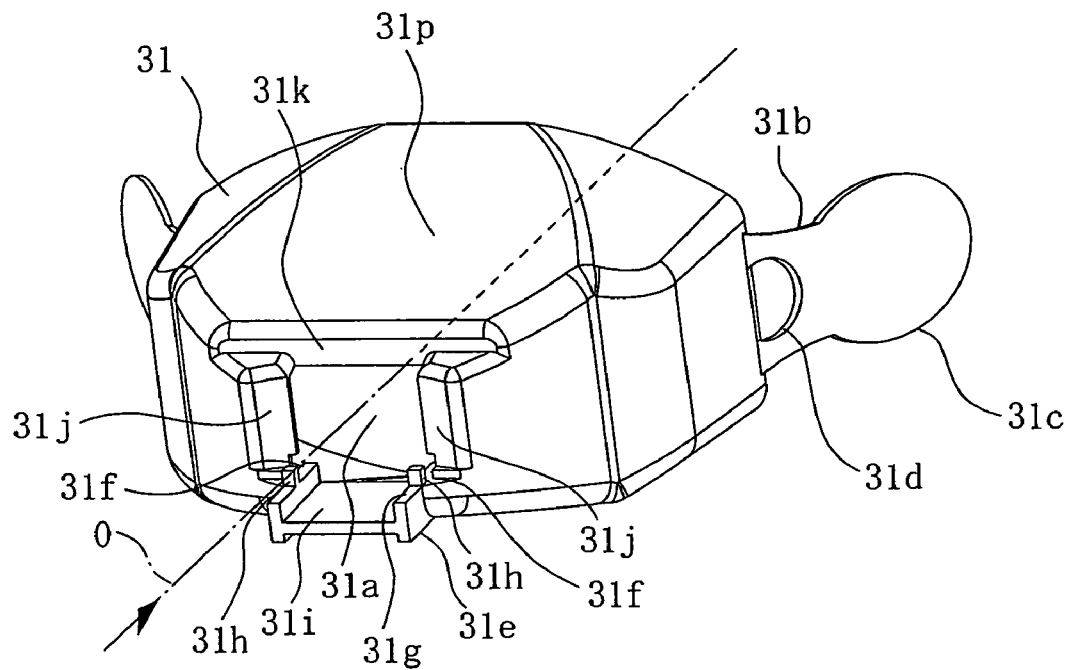
FIG. 10 is an oblique perspective diagram of a contact cap for dental tooth measuring attached to the top cover of FIG. 3.
Figure 11:
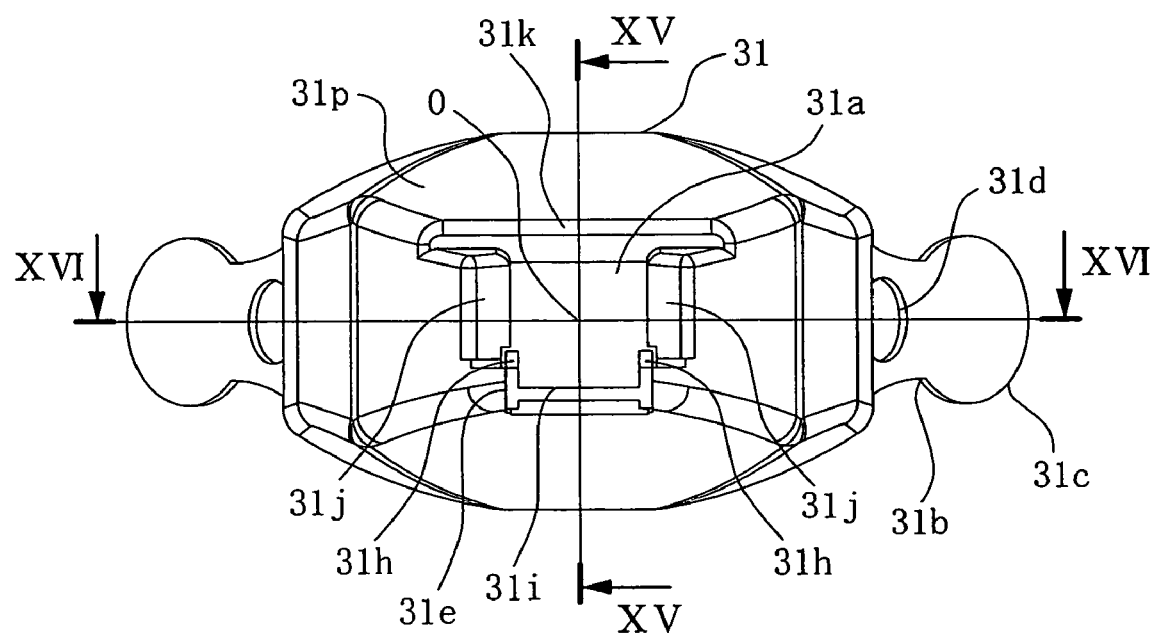
FIG. 11 is a front view of the contact cap of FIG. 10.
Figure 12:
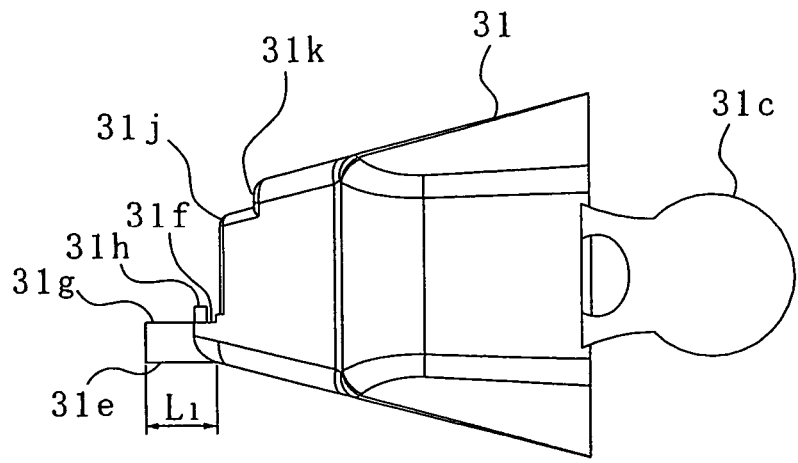
FIG. 12 is a side view of the contact cap of FIG. 10.
Figure 13:
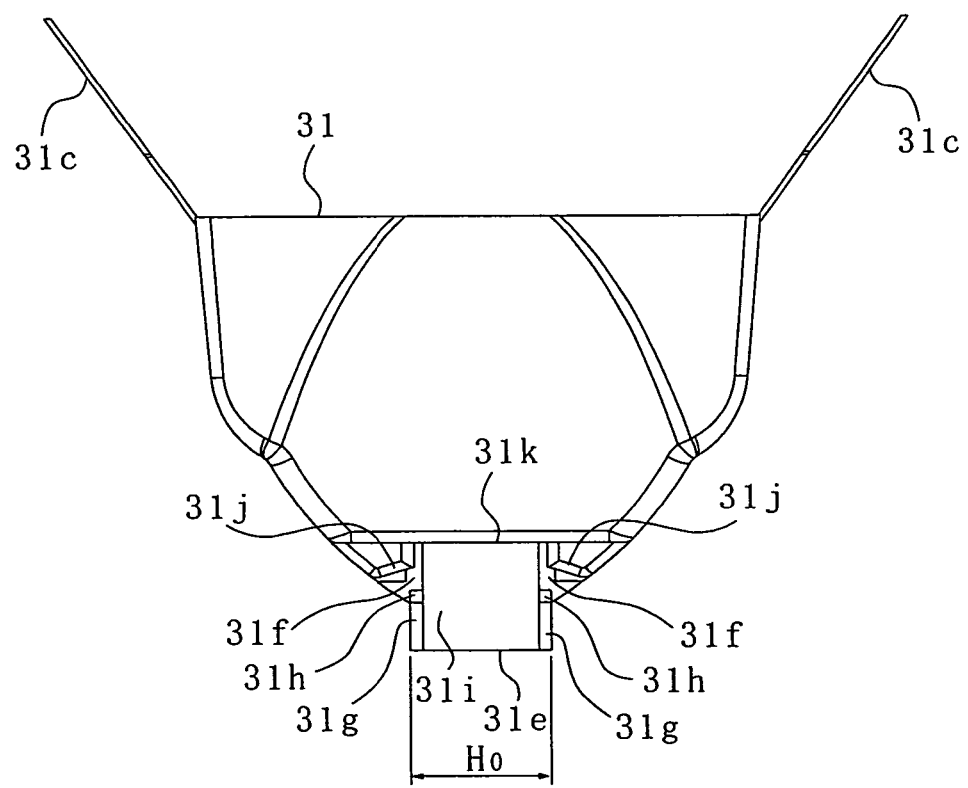
FIG. 13 is a plan view of the contact cap of FIG. 10.
Figure 14:
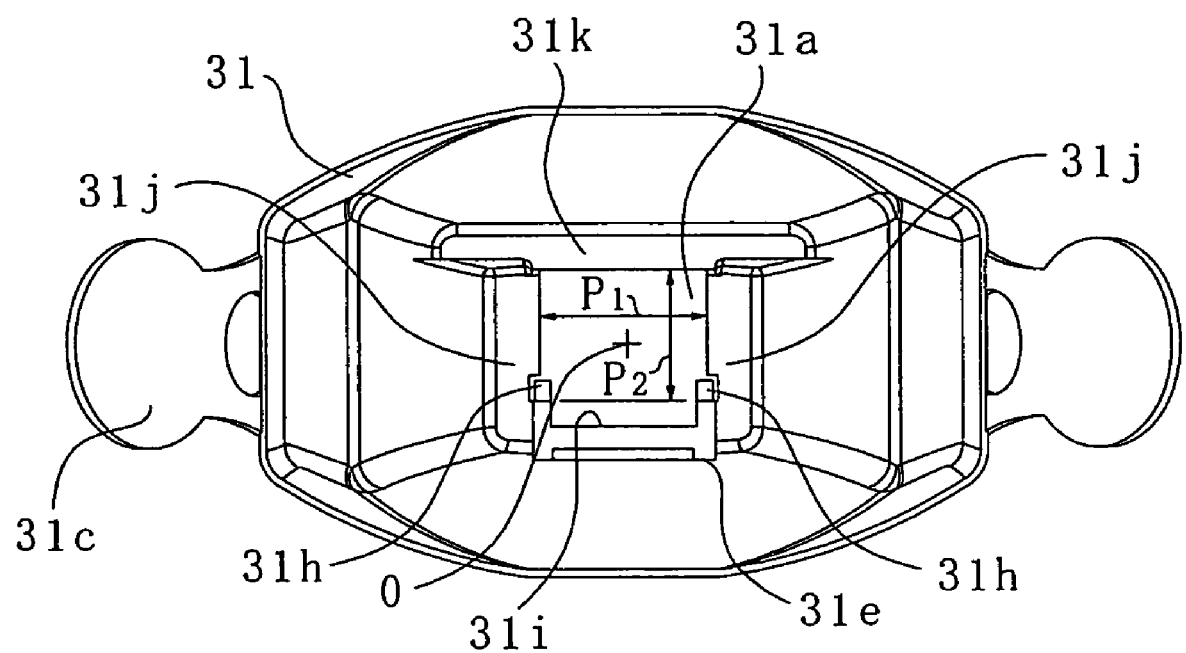
FIG. 14 is a back view of the contact cap of FIG. 10.
Figure 15:
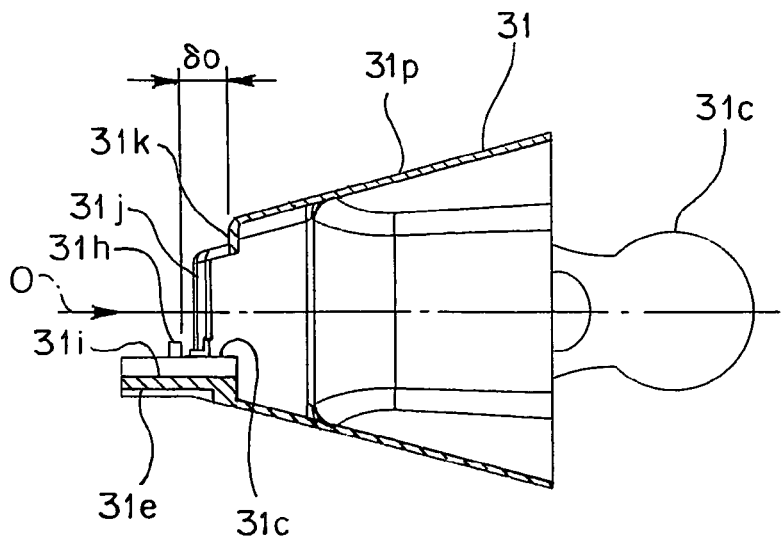
FIG. 15 is a XV-XV cross sectional diagram of FIG. 11.
Figure 16:
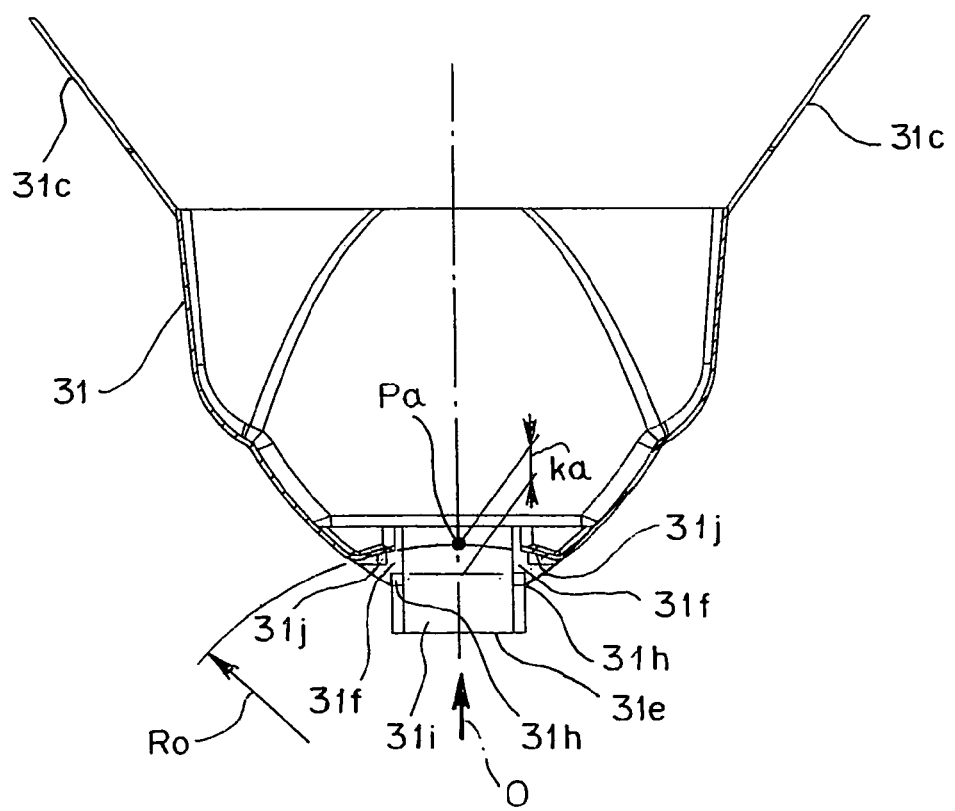
FIG. 16 is a XVI-XVI cross sectional diagram of FIG. 11.

FIGS. 10 to 16 are figures showing appearances or cross-sectional shapes of the contact cap: FIG. 10 is an oblique perspective diagram of the contact cap, and FIG. 11 is a front view of the contact cap. FIG. 12 is a side view of the contact cap. FIG. 13 is a plan view of the contact cap. FIG. 14 is a back view of the contact cap. FIG. 15 is a XV-XV cross-sectional diagram of FIG. 11. FIG. 16 is a XVI-XVI cross-sectional diagram of FIG. 11.

The contact cap 31 is a member in a shape of a thin-walled cap made from materials such as black elastic synthetic resin rubber, for example, styrene elastomer, and used as being laid over the external front of the top cover 12 of the camera 2 (FIGS. 4, 17). The material with around 70 degrees in rubber hardness of the material is applied from the viewpoint of fitness and attachment (with a tolerance level between 50 degrees to 80 degrees). The contact cap 31 is a disposable type to be discarded after used for hygienic reasons.

Provided for the contact cap 31 are; a cap section 31p to be attached to cover the top cover 12 at the front, a central opening section 31a which is a shooting window section 12a to be placed in the central place of the optical axis O in the front of the shooting optical system 18 in an attached state at the front side of the cap, a front upside section 31k which forms the upside of the opening section 31a, a bite section 31e as a protrusion section to be placed as being sticking out ahead in the direction of the optical axis O below the opening section 31a, a flexible membranous wall section 31j forming both left and right sides of the opening section 31a, and extending sections 31b for extending backward to the left and the right of the cap section 31p in parallel with the direction of the optical axis O.

The inside of the cap section 31p is grained for the purpose of preventing reflection. The shape of the inside of the cap section 31p is vertically and horizontally symmetrical and can be attached to the top cover 12 even when it is upside down.

Although the details will be described later, in the state of shooting a tooth to be measured 51 (for example, an incisor), the bite section 31e is slightly bitten by the adjacent teeth sandwiching the tooth to be measured 51 with the contact cap 31 laid over the top cover 12 of the camera 2. Then, the tooth to be measured is positioned near the central section of the opening section 31a with the outside light being shielded, and shot by the image capturing section 19 placed inside the camera 2.

The size of the central opening section 31a of the contact cap 31 is about 16 mm for the left to right width P1 and about 14 mm for the top to bottom length P2 as shown in FIG. 4 (it is the length to the upside section 31f of the bite section 31e and the length to the concave section 31i of the bite section 31e is 16 mm). The size includes a part of adjacent teeth of the tooth to be measured 51 of an object of shooting, assuming that the tooth is the incisor of a usual adult incisor with the upper limit of about a square of 10 mm. As the opening section 31a is set bigger than the tooth to be measured 51, it is prevented from making surrounding of the objective tooth dark as the objective tooth is hidden behind the opening section from the LED illumination system which illuminates the tooth. Then, it is set so that the penetrating outside light is reduced while the influx of breath from the inside of the patient's mouth being restricted as much as possible and affection to shot images surrounding the opening section 31a of the black cap section being reduced. It is certainly possible, however, to prepare another size of the opening section 31a for a special case.

The bite section 31e of the contact cap 31 is placed below the opening section 31a as shown in FIGS. 10, 11 and the like and has a channel shape (in a channel state) or a U shaped cross sectional shape which sticks out ahead in parallel with the optical axis O. The bite section 31e has a concave section 31i, right and left upside sections 31f as biting sections rising from the concave section 31i forming the right and left channel upsides, and right and left upside sections 31g of a front extending section, as well as a pillar convex section 31h of right and left positioning convex sections placed on the upside section 31f for positioning the tooth to be measured 51 in the direction of the optical axis O.

Figure 19:
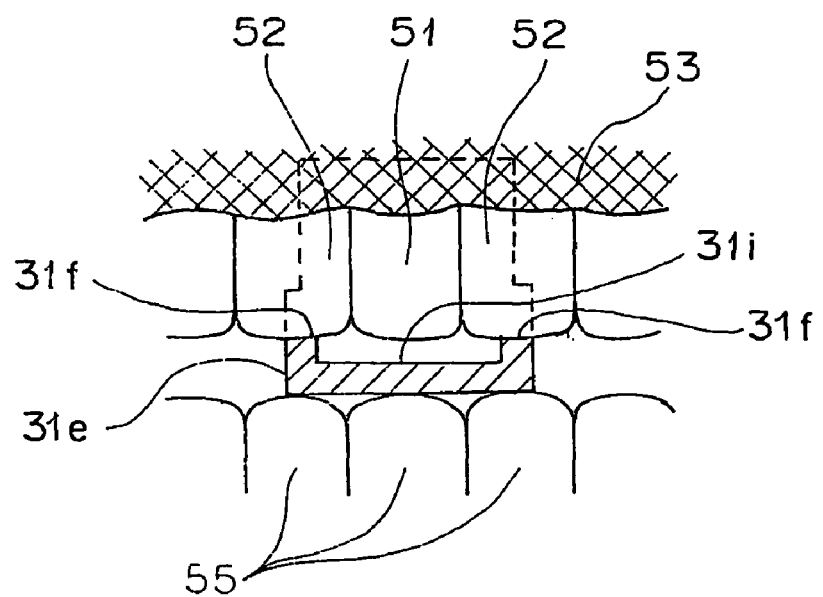
FIG. 19 is a XIX-XIX cross sectional diagram of FIG. 17.

As the bite section 31e is bitten by teeth, the tooth to be measured 51 is positioned. That is to say, the tooth, for example the lower tooth 55, opposite to the tooth to be measured 51, for example an incisor, is applied to the bottom of the bite section 31e and adjacent teeth 52 sandwiching the incisor are inserted from upside at the backside (front side from the viewpoint of the patient) of the pillar convex section 31h at the same time as shown in FIGS. 17, 19 to be described later when the tooth is being shot. Then, the upside section 31f is slightly bitten as the inside of the adjacent teeth 52 are applied to the backside of the pillar convex section 31h. The incisor of the tooth to be measured 51 is positioned at the central section of the opening section 31a in the direction of the optical axis O as biting, and placed at the best focus position (slightly slide according to a difference in teeth shapes).

The width H0 of the bite section 31e (outside width, FIG. 13) is preferably a size that can be bitten by the adjacent teeth 52 and near to the opening width P1, but can be applied in a range around 12 mm to 20 mm.

The length L1 of the bite section 31e (FIG. 12) is set around 14 mm and adapted to be easily inserted in the buccal cavity and not make a tongue affect the shooting screen as the tongue is inserted.

Figure 18:
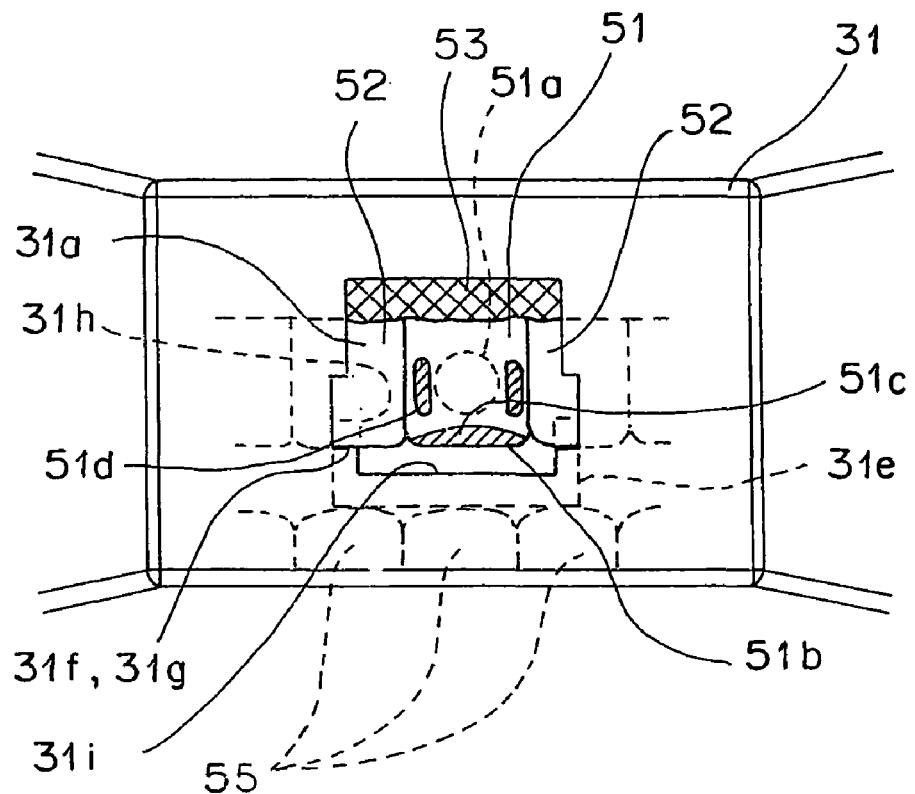
FIG. 18 is a view seen from the E arrow of FIG. 17.

For the step (concave amount) between the upside section 31f and the concave section 31i, about 2 mm is adopted, and a gap between the cutting edge section (tip section) 51b of the tooth to be measured 51, for example an incisor, and the concave section 31i in the above described biting state is kept to 1.5 mm or more (FIGS. 17, 18).

As the gap is provided, vignetting of the images surrounding the cutting edge section 51b is prevented as to be described later.

The pillar convex section 31h can be easily elastically distorted and may also be adjusted to a change in thickness of the adjacent teeth or a torsion tooth, a bicuspid tooth without preventing freedom as the shooting direction of the camera 2 is changed.

The wall section 31j of the contact cap 31 is formed by a part of right and left membranous two cylinder surfaces, which are easily distorted and protruding ahead from the position of the front upside section 31k. The wall section 31j is placed near a position opposite to both of the adjacent teeth 52. The wall section 31j is placed at a predetermined distance of a space section on the upside section 31f of the biting section from the backside place of the pillar convex section 31h as a gap so that the adjacent tooth 52 can be inserted with a certain degree of freedom at shooting. The place of arrangement is set in association with the width (outer width) of the bite section 31e, the curvature radius of a row of teeth including the tooth to be measured and thickness of the tip section of the teeth as to be described later.

An appropriate arranged place of the wall section 31j will be described with reference to a plan arrangement diagram showing a curvature radius of a row of teeth and a range for wall section arranged place against the bite width in the contact cap 31 of FIG. 21.

The wall section 31j has flexibility as mentioned above. If the inclination and position of the tooth to be measured are adjusted at measuring the tooth to be measured, the inclination and place can be adjusted as the adjacent teeth 52 contacts and dents the wall section 31j, though, its movable amount is limited. Then, a predetermined gap (a space region given by the upside section 31f) is provided between the pillar convex section 31h and the wall section 31j. Accordingly, in a usual measuring state (shooting a tooth to be measured of a usual size), the adjacent tooth 52 is preferably inserted with a slight gap without distorting the wall section 31j. If the gap is too big, the outside light comes into the shooting optical system 18 and adversely affects the shot data, thus, the arrangement should be performed suitably. If the tooth to be measured inclines to the jaw, the abovementioned adjustment of inclination of the tooth to be measured at shooting is necessary adjustment to incline the tooth to be measured against the optical axis O to acquire accurate shooting data to be described later.

The variation among individuals of the curvature radius of a row of teeth including the tooth to be measured 51 and the adjacent teeth 52 is examined, assuming that an incisor is selected as the tooth to be measured 51 as mentioned above, with a result for the rows of teeth of 126 people, the minimum curvature radius Ra (outside) Ra being 23 mm and the maximum curvature radius (outside) Rb being 36 mm. Therefore, the row of teeth to be measured generally provided for measurement can be determined in the range of the minimum curvature radius Ra=23 mm to the maximum curvature radius Rb=36 mm.

The thickness of the tip of the adjacent teeth 52 is examined, with a result of the average thickness of the tip of a part corresponding to the height of the pillar convex section 31h being about 1.5 mm and the upper limit of the thickness b0 being 2.5 mm.

The width H0 of the bite section 31e (outside width) is assumed to adopt the range of 12 mm to 20 mm as mentioned above.

Assuming that the bite section 31e with the width H0 is bitten by the row of teeth with the minimum curvature radius Ra or the maximum curvature radius Rb with the thickness of tooth tip b0 and the inside of the adjacent teeth 52 is applied to the pillar convex section 31h, the state will be that shown in FIG. 21.

Here, pa in the figure represents a point on the La line normal to the optical axis O which passes the intersection point of the front edge (from the viewpoint of a patient) of the tooth to be measured 51 with the minimum curvature radius Ra and the optical axis O, the point pb represents a point on the Lb line normal to the optical axis O which passes the intersection point of the front edge of the tooth to be measured 51 with the maximum curvature radius Rb and the optical axis O. The distance between the point pa (on the La line) which gives the front edge position of the tooth to be measured 51 with the minimum curvature radius Ra and the pillar convex section 31h is shown by the distance Ka in the figure. On the other hand, the distance between the point pb (on the Lb line) which gives the front edge position of the tooth to be measured 51 with the maximum curvature radius Rb and the pillar convex section 31h is shown by the distance Kb in the figure. It is a matter of course that Ka>Kb, and the row of teeth of the teeth to be measured 51 with the minimum curvature radius Ra is placed backward at the camera side (ahead from the viewpoint of a patient) than those with the maximum curvature radius Rb.

Therefore, a region where the wall section 31j is to be placed is preferably a cylinder surface region S0 of the curvature radius R0 bigger than the curvature radius Ra passing the point pa which is separated by the distance Ka to backward at the camera side (front from a viewpoint of a patient) from the pillar convex section 31h. As the curvature radius R0, the maximum curvature radius Rb is preferably adopted.

As the curvature radius R0, the maximum curvature radius Rb is preferably adopted. That it to say, "a predetermined gap" between the positioning convex section and the wall section 31j can be set based on the distance Ka between the point pa on the La line and the pillar convex section 31h, and a cylinder surface with a center on the optical axis O and passes the point pa with the maximum curvature radius Rb.

If the abovementioned bite section 31e has the bite width H0=12 mm, the specific position of the wall section 31j is placed along the cylinder surface formed by the curvature radius Rb=36 mm (the center is on the optical axis O) passing the point pa which is separated from the pillar convex section 31h by the distance Ka=3.4 mm.

On the other hand, if the bite section 31e has the bite width H0=20 mm, the wall section 31j is placed along the cylinder surface formed by the curvature radius Rb=36 mm passing the point pa which is separated from the pillar convex section 31h by the distance Ka=5.1 mm.

If the size between 12 to 20 mm is adopted as the bite width H0 of the bite section 31e, the distance Ka of the pillar convex section 31h is obtained by $$Ka = b0 + (Ra - b0) \times (1 - \cos(\sin^{-1}((H0/2)/(Ra - b0)))) \tag{1}$$

It is preferable that the curvature radius R0 of the wall section 31j passing the point pa similarly adopts a value of the Rb.

The "predetermined gap" between the positioning convex section and the wall section 31j is a gap between the wall section 31j and the pillar convex section 31h (separated distance) D (FIG. 22), represented by the expression below.

$$D=b0+(Ra-b0)\times(1-\cos(\sin^{-1}((H0/2)/(Ra-b0))))-Rb\times(1-\cos(\sin^{-1}((H0/2)/Rb)))\quad(2)$$

When the thickness of the tooth tip b0 is 2.5 mm, the minimum curvature radius Ra is 23 mm, and the maximum curvature radius Rb is 36 mm and the bite width H0 is 12 mm, the gap D is 2.9 mm. If the bite width H0 is 20 mm, the gap D is 3.7 mm.

By setting the minimum curvature radius Ra and the maximum curvature radius Rb as mentioned above, a predetermined gap between the pillar convex section 31h and the wall section 31j is a distance for a tooth generally provided for measurement to be inserted comfortably and possible to be positioned.

As various shapes of the wall section 31j in the contact cap of the embodiment applied with the conditions, those shown in a plan view of the wall section 31j against the pillar convex section 31h of FIG. 22 to FIG. 25 can be proposed.

Figure 22:
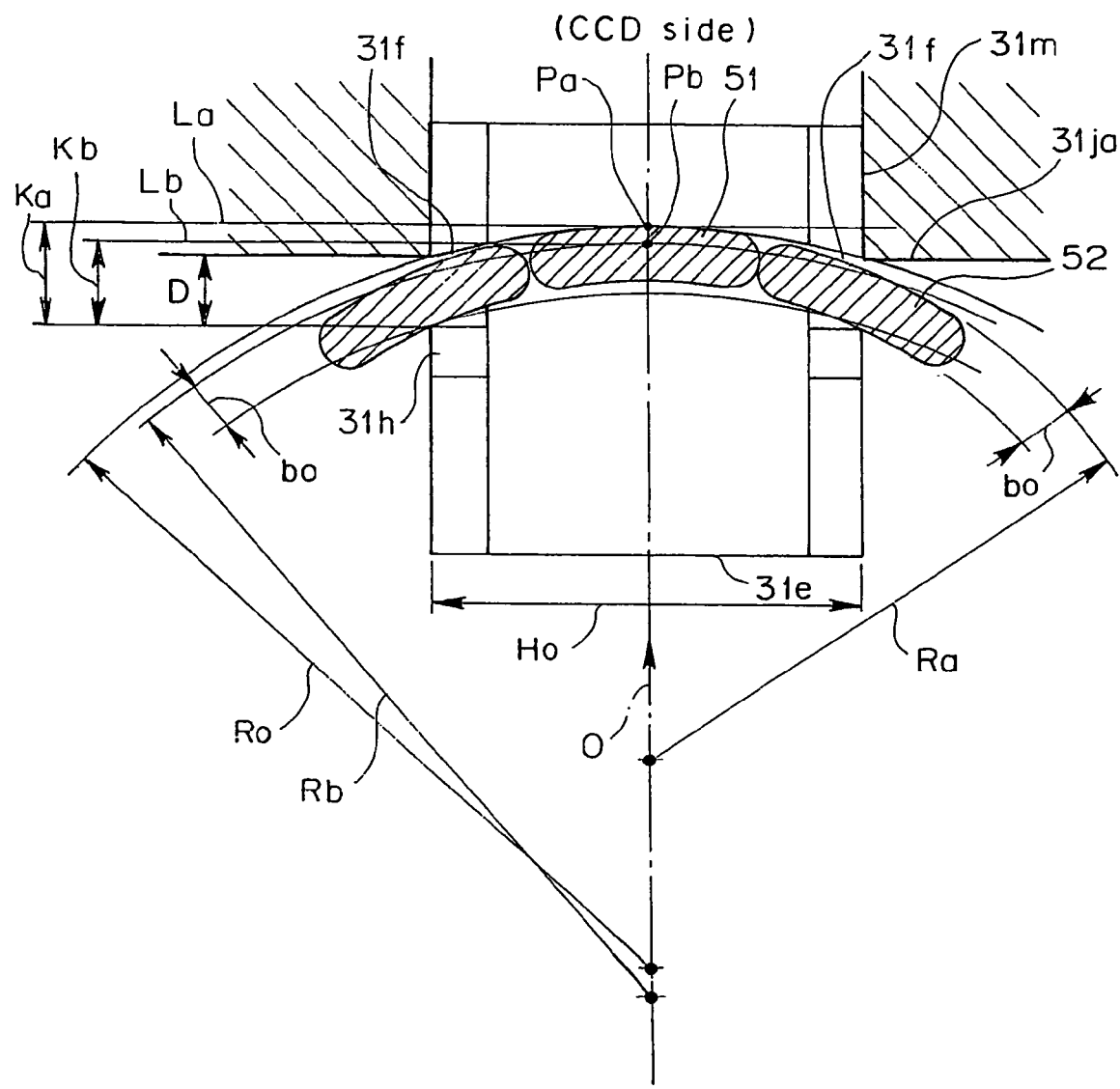
FIG. 22 is a plan arrangement view showing an example of a shape of a wall section in the contact cap of FIG. 10.

First, that shown in FIG. 22 as a usual example is for the case where the bite width H0 is 16 mm, the wall section 31ja is assumed as a plain orthogonal to the optical axis O and the gap D against the pillar convex section 31h is 3.2 mm. It is not limited to the plain shape in the example of the wall section 31ja, and it can be changed in the cylinder surface region S0 shown in abovementioned FIG. 21 with a section fulfilling the abovementioned conditions.

Figure 23:
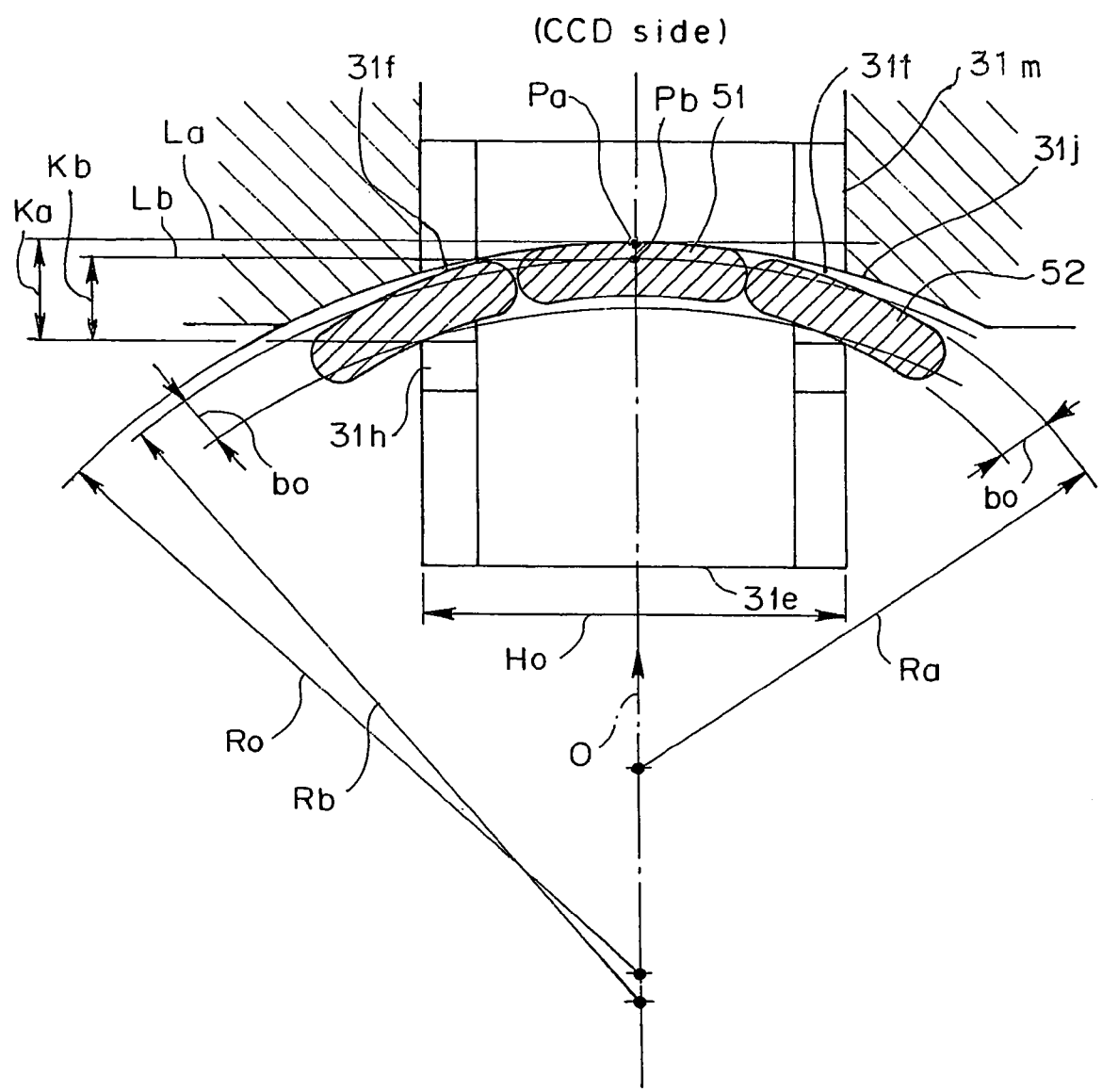
FIG. 23 is a plan arrangement view showing another example of a shape of a wall section in the contact cap of FIG. 10.

For example, the wall section 31j can be formed in a shape bending along the row of teeth while fulfilling the conditions as shown in FIG. 23. Accordingly, as the surface of the wall section 31j contacts the surface of the teeth, an operator can smoothly apply the cap 31p to the patient. The cap section 31p can be more softly applied to the patient. In such a case, the inside 31m of the wall section 31j forming the opening section (opening window) 31 matches the bite width.

Figure 24:
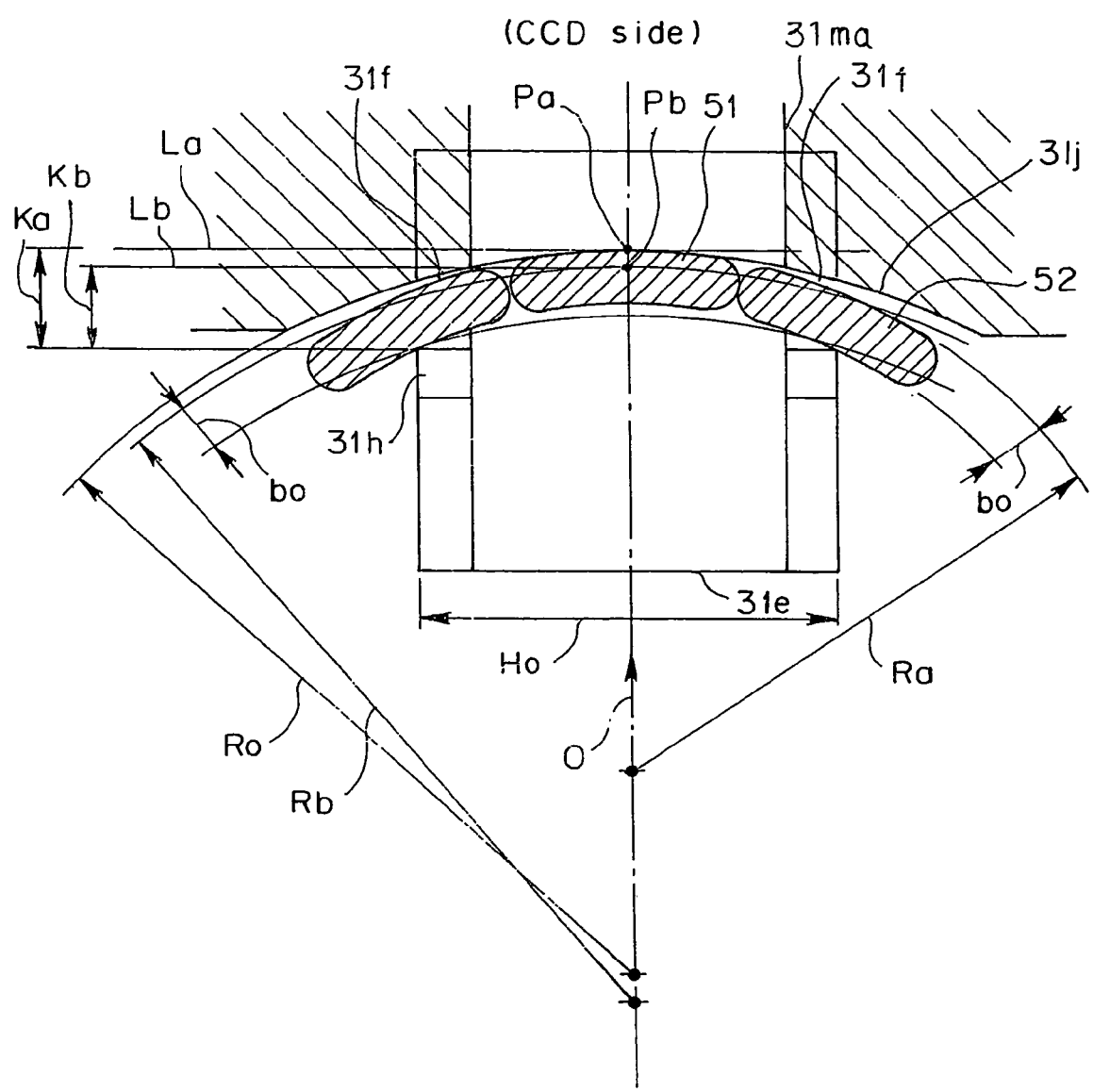
FIG. 24 is a plan arrangement view showing yet another example of a shape of a wall section in the contact cap of FIG. 10.

As shown in FIG. 24, the wall section 31j may have a shape formed by a bending surface with a wall inside 31ma a little bit tapering the opening section (opening window) 31a inside while fulfilling the conditions. Opening section 31a prevents the outside light from coming inside and the measurement can be more stabilized.

Figure 25:
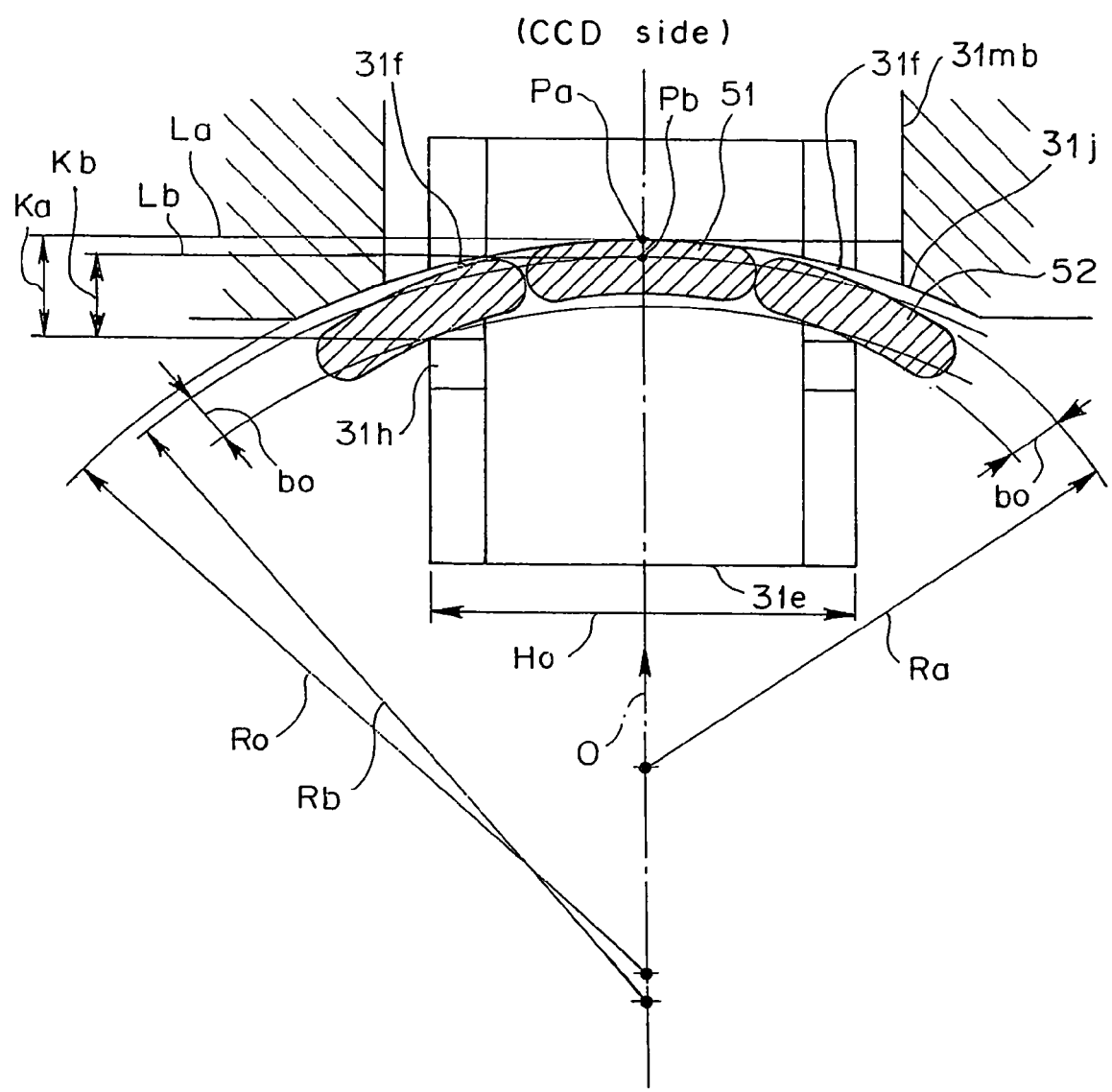
FIG. 25 is a plan arrangement view showing yet another example of a shape of a wall section in the contact cap of FIG. 10.

Further, as shown in FIG. 25, the wall section 31j may have a shape with the wall inside 31mb with the opening section (opening window) 31a wider than the bite width, while fulfilling the conditions. That makes a patient's tooth whose width is much bigger than usual can be measured.

As the contact cap 31 is attached, the best focus position P0 of the shooting optical system 18 of the camera 2 is set in consideration of an average tooth thickness, assuming the best focus position P0 is ahead the position of the point pa (the side of the tooth to be measured) in FIG. 21.

The front upside section 31k of the contact cap 31 contacts the top section 12d of the top cover 12 being attached to the inside of the contact cap 31. The front upside section 31k is at a distance of δ0 from the backside of the pillar convex section 31h (FIG. 15), and when the bite section 31e is bitten at shooting, it is at a distance from a gum section 53 upward the tooth to be measured 51. Therefore, even if the tooth to be measured 51 is inclined at shooting, the front upside section 31k never contacts the gum section 53 (FIG. 17).

Each of the two extending sections 31b of the contact cap 31 is formed with elastic thinness provided with a latch hole 31d which can latch a latching protrusion 12f of the top cover 12 (FIG. 6) and a pinch section 31c at the tip section (FIG. 10). When the latch hole 31d latches the latching protrusion 12f of the top cover 12 as the pinch section 31c is pulled with the contact cap 31 being laid over the top cover 12, the contact cap 31 is attached to the top cover 12 to be able to shoot. The contact cap 31 is assumed to be discarded after used once for hygienic reasons, and the used one is in a state where the extending section 31b stays extended or in a state where it cannot be reused as it breaks when the latch is released or the like.

Next, an operation for shooting (measuring) the tooth to be measured 51 by attaching the contact cap 31 to the camera 2 with the abovementioned configuration will be described with reference to FIGS. 17 to 20 and FIG. 26.

FIG. 17 is a diagram showing a single tooth (tooth to be measured) is shot in the measurement shooting mode on the XV-XV cross-section of FIG. 11, showing a normal shooting state where the upper incisor (tooth to be measured) is placed and shot at the opening section of the contact cap. FIG. 18 is a view seen from the E arrow of FIG. 17. FIG. 19 is a XIX-XIX cross-sectional diagram of FIG. 17. FIG. 20 is a diagram seen from the E arrow of FIG. 17, showing the tooth to be measured is too much inclined to the optical axis O.

If shooting is performed assuming that the tooth to be measured 51 of the upper incisor (vital tooth) is a single tooth by attaching the contact cap 31 to the camera 2, first, the cap section 31p of the contact cap 31 is laid over the top cover 12 and the contact cap 31 is attached to the camera 2 as shown in FIG. 4 and latched.

The bite section 31e of the contact cap 31 as being attached is inserted in the buccal cavity of the patient, lower teeth 55 is applied to the bottom of the bite section 31e, and the inside of the adjacent teeth 52 adjacent to the incisor 51 is applied to the backside (front side from a viewpoint of a patient) of the pillar convex section 31h of the bite section 31e. The upside section 31f is slightly bitten at the tip of the cutting edge so as not to distort it too much (FIG. 19). In such a state, the tooth to be measured 51 is placed at the best focus position of the shooting optical system 18 of the camera 2, and shooting of the incisor 51 by the camera 2, i.e., multi-band shot image data measurement is performed.

There is variation among individuals for the curvature radius of the row of teeth including the tooth to be measured (incisor) 51 and the adjacent teeth 52 and the thickness of the teeth tip as mentioned above, the place of the front (from a viewpoint of a patient) of the tooth to be measured 51 against the shooting optical system 18 in the direction of the optical axis O changes by the variation among individuals even if the adjacent teeth 52 of the pillar convex section 31h of the bite section 31e contacts. Specifically, assuming that the place of the tooth to be measured 51 shifts 1.1 mm due to a change in the curvature radii Ra, Rb of the row of teeth and also shifts 1 mm due to thickness of the teeth tip b0, it may shift 2.1 mm in total.

Figure 26:
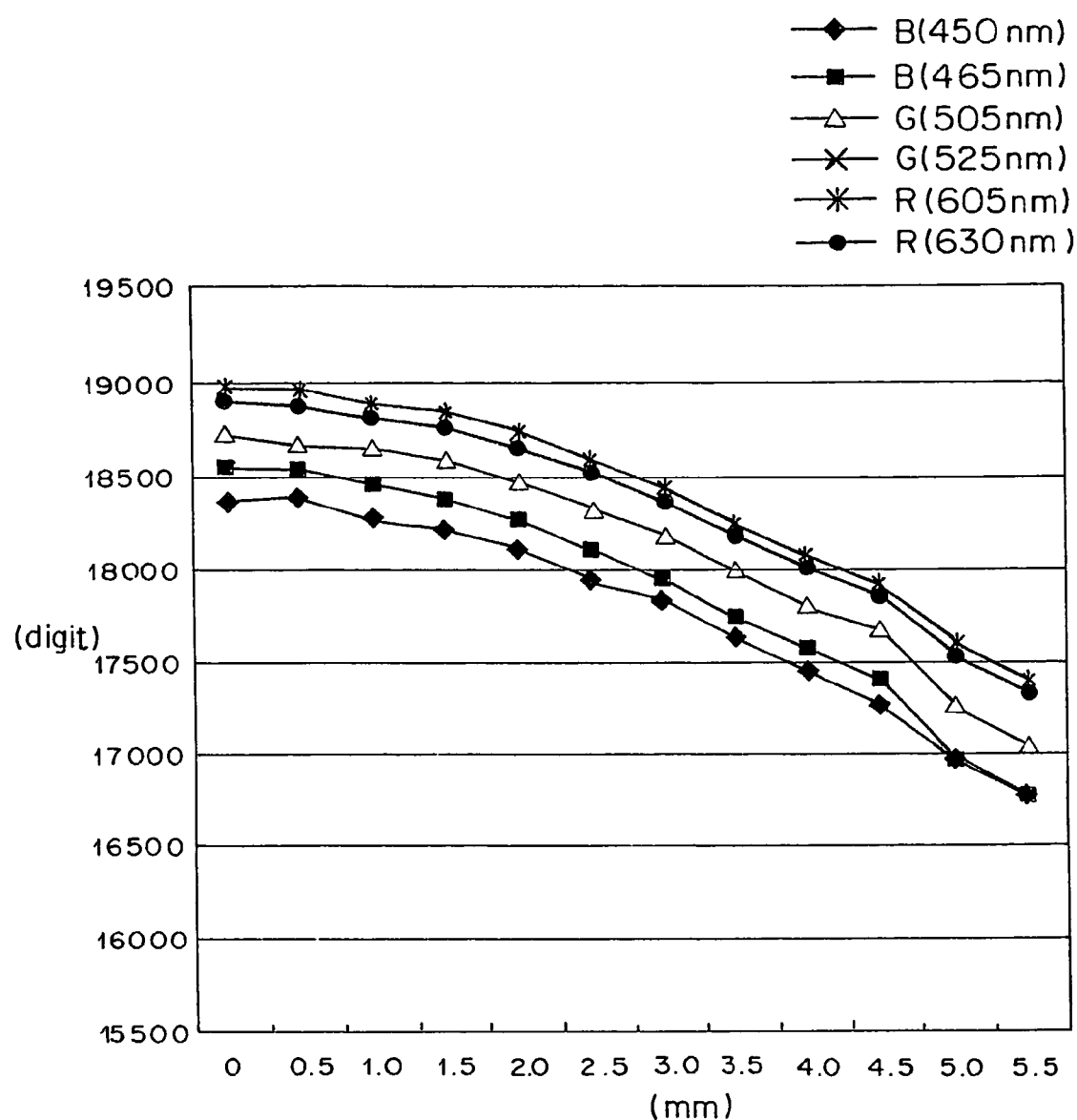
FIG. 26 is a diagram showing a change in RGB signal values of a shot image against a change in a distance in the direction of an optical axis of the tooth to be measured in the camera of FIG. 3.

FIG. 26 is a diagram showing a change in RGB signal values of a shot image against a change in a distance in the direction of an optical axis O of the tooth to be measured 51 in the camera 2. In the figure, assuming that the place at the distant 1 mm is the best focus position of the shooting optical system 18, it is in a permissible range determined by a change in RGB signal values of a shot image shown in FIG. 26 even with a shift from the place about ±1 mm. Therefore, even if the tooth to be measured 51 shifts by 2.1 mm as mentioned above, shot data with accuracy of a permissible range can be captured without adjusting a focus at shooting.

On the other hand, in the abovementioned state where the bite section 31e is bitten, the outside light is certainly shielded by the wall section 31j or the like from surrounding of the incisor, which is a tooth to be measured 51. Then, the incisor 51 is fixed to the front section of the opening section 31a near the optical axis O in the center of the opening section 31a (FIGS. 18, 19), and the shooting optical system 18, the image capturing section 19 of the camera 2 can be correctly positioned in the direction of the optical axis O and the orthogonal direction of the optical axis O. As a transparent cutting edge 51a of the tip of the incisor 51 is kept with a predetermined gap with respect to the concave section 31i of the bite section 31e, an image of the cutting edge is prevented from being darker (FIG. 18). If the cutting edge section 51b closely approaches or touches the concave section, the cutting edge section 51b is shaded as the light is vignetted or saliva penetrates into the gap and shooting may not be performed correctly, however, that can be prevented.

The gum section 53 upper the incisor 51 is neither whitened due to lack of a blood flow as it does not contact the front upside section 31k nor adversely affects a shot image of the incisor 51. Further, the cap section 31p can be applied to the patient more softly.

The shooting state of the tooth to be measured 51 shown in FIG. 18 is in a state where the center surface of the tooth to be measured 51 is about orthogonal to the optical axis O. Then, as the regular reflection regions 51c, 51d, which are parts for regularly reflecting to both sides, are separated from the center measured part of the teeth to be measured 51 by almost equal distances, accurate shot image data can be captured.

If the tooth to be measured 51 is extremely inclined to the optical axis O, however, the regular reflection region 51c' penetrates into the center measured part 51a of the teeth to be measured 51 as shown in FIG. 20, thus, accurate shot data cannot be acquired. In such a state, in case of the embodiment, a person who shoots (measures) adjusts the regular reflection region 51c to be placed at both sides at a distance from the center measuring section 51a as shown in FIG. 18 by changing the direction of the camera 2, while observing the shot image of the tooth to be measured 51 in which the regular reflection region 51c' is shot. After the adjustment, shooting can be performed and accurate shot image data can be acquired.

If the direction of the camera 2 is changed as mentioned above, the contact cap 31 can easily adjust the direction of the camera 2 as there is a gap between the adjacent teeth 52 and the wall section 31j. If the thickness of the adjacent teeth 52 is quite thick or the inclination of the camera 2 needs to be changed extremely, the wall section 31j of the contact cap 31 has flexibility. Therefore, inclination adjustment in a wider range can be performed by deforming the wall section 31j.

The head of the patient needs to be somewhat supported so as not to move during the shooting. As the bite section 31e is bitten by the upper and lower teeth, the incisor 51, which is a tooth to be measured, is kept in a state where the incisor 51 and the opening section 31a cannot be relatively moved in the direction of the optical axis O and the top to bottom and the right to left (state of not easily shifted).

Therefore, the strength to fix the head of the patient during the abovementioned shooting does not need to be strong too much.

If the lower teeth 55 (for example, a lower incisor) is shot by using the contact cap 31, shooting is performed as the contact cap 31 is placed in the reverse directions and attached to the top cover 12. In such a case, the upper teeth bites the bottom side of the bite section 31e, and the lower teeth 55 adjacent to both sides of a particular lower tooth 55, which will be a tooth to be measured, slightly bites the upside section 31f, and the particular lower tooth 55, which will be the tooth to be measured, is placed at the center place of the central opening section 31a and at the front of the opening section in the direction of the optical axis O. That can cause the particular lower tooth 55 to be shot with the outside light being certainly shielded similar to the above description. In such a case, the cutting edge of the particular lower tooth 55 is placed with a predetermined gap with respect to the concave section 31i and can capture accurate shot image data.

The contact cap 31 is formed by a black material, efficiently absorbs the outside diffused lights as the entire of the inside is grained, and is also effective in absorbing stray lights so that accurate color measurement result (shot image data) can be acquired without any uncomfortable appearance occurs in the shot image. Particularly inside the cap surrounding the central opening section 31a or inside the cap corresponding to the notch section 12c ahead the top cover 12 (FIG. 3), a LED light is applied to. As the surfaces are black and grained as mentioned above, regular reflection is avoided and the inside diffused lights are alleviated.

The contact cap 31 easily attached to and detached from the top cover 12 at the camera side as it is made from a cap material with elastic thinness. That is to say, after the cap 31 is laid over the top cover 12, the extending sections 31b at both sides are extended and easily latch the latching protrusion 12f to be attached.

As the tip section of the adjacent teeth 52 at both sides of the tooth to be measured 51 is positioned by being contacted the pillar convex section 31h for positioning the contact cap 31, positioning for shooting becomes easier and accuracy of color measurement, reproducibility and speed in a shooting operation improve. As positioning is performed with the adjacent teeth 52 adjacent to the tooth to be measured 51, components for positioning little affect the accuracy of color measurement of the tooth to be measured. The pillar convex section 31h for positioning is easily bent as it is bitten, and can be positioned by a torsion tooth or a bicuspid tooth.

The biting section of the bite section 31e is in a channel state or in a shape of U. Thus, when the upper tooth is measured, shooting can be stably performed without a camera shake as an upper adjacent tooth and the lower tooth bite the bite section. At the same time, as the cutting edge of the tooth to be measured is kept with a gap with respect to the concave section 31i of the bite section, the light beam is not vignetted around the tip of the cutting edge and saliva does not penetrate into the tip of the cutting edge. That can improve a phenomenon of the tip of the cutting edge being darker.

Further, the gum section 53 upper the tooth to be measured 51 does not contact the front upside section 31k upper than the opening section 31a of the contact cap 31. Therefore, blood flow of the upper gum section 53 can be stopped and prevented from being whitened, and the shot image data (color measured data) of the tooth to be measured is never affected.

As the camera 2 with the contact cap 31 being attached has the bite section 31e or the like of the cap 31 protruding outside, it cannot be attached to the cradle 1 as shown in FIG. 1 so that any erroneous operation with the cap being attached to the camera 2 is prevented in advance.

When the contact cap 31 is attached to the top cover 12 of the camera 2, the camera 2 is protected from dirt, an external strength or the like in at least a range covered by the cap 31.

As mentioned above, according to the present invention, the contact cap for the dental tooth measuring which can acquire more correct measurement result can be provided by causing the objective tooth to be measured to be positioned at the stable shooting position in the dental tooth measuring apparatus. It also provides a measuring method which enables accurate measurement by the dental tooth measuring apparatus.

The present invention is not limited to each of the abovementioned embodiments, and various modifications can be implemented in a range without departing from the spirit of the invention in implementing stages. Further, each of the abovementioned embodiments includes various stages of inventions so that various inventions can be extracted by appropriately combining a plurality of components to be disclosed.

For example, if problems described in the "problems to be solved by the invention" can be solved and an effect described in the "advantages of the invention" is acquired when some components are deleted from all components shown in each of the embodiments, the configuration with the components deleted can be extracted as the invention.

What is claimed is:

1. A contact cap for a dental tooth measuring apparatus comprising:
    a cap section which is attachable to cover a periphery of a shooting window section of the tooth measuring apparatus;
    an opening section which has a size to include a tooth to be measured and parts of a pair of adjacent teeth adjacent to the tooth to be measured, wherein the opening section is arranged before the cap section, and faces the shooting window section when the cap section is attached to the tooth measuring apparatus;
    a protrusion section which is placed below the opening section so as to protrude ahead of the tooth measuring apparatus, and which is biteable by the pair of adjacent teeth;
    a pair of pillar convex sections formed on an upper portion of the protrusion section for positioning tongue sides of the pair of adjacent teeth, wherein the pair of pillar convex sections are arranged separately from each other; and
    a wall section which is provided on the cap section and which is placed with a predetermined gap at a side of the tooth measuring apparatus with respect to the pair of pillar convex sections.

2. The contact cap according to claim 1, wherein the wall section is formed by an elastic material.

3. The contact cap according to claim 1, wherein the wall section is placed at a position corresponding to a width of the protrusion section, the width of the protrusion section is 12 mm, and the wall section is placed substantially on a cylinder surface passing a position on an optical axis behind the pair of pillar convex sections by 3.4 mm.

4. The contact cap according to claim 1, wherein a predetermined gap D mm between the wall section and the pair of pillar convex sections is given by $$D=2.5+(23-2.5)\times(1-\cos(\sin^{-1}((H0/2)/(23-2.5))))-36\times(1-\cos(\sin^{-1}((H0/2)/36)))$$

where H0 is a width of the protrusion section, and where 12 mm≦H0≦20 mm.

5. A method for measuring a tooth by a dental tooth measuring apparatus attached with a contact cap, the method comprising:
    inserting the contact cap into a buccal cavity of a patient, wherein the contact cap includes: (i) a cap section which is attachable to cover a periphery of a shooting window section of the dental tooth measuring apparatus, (ii) an opening section which is arranged before the cap section and which faces the shooting window section when the cap section is attached to the tooth measuring apparatus, (iii) a protrusion section which is placed below the opening section so as to protrude ahead of the dental tooth measuring apparatus and which is biteable by a pair of adjacent teeth adjacent to the tooth to be measured, (iv) a pair of pillar convex sections formed on an upper portion of the protrusion section for positioning tongue sides of the pair of adjacent teeth, wherein the pair of pillar convex sections are arranged separately from each other, and (v) a wall section which is provided on the cap section and which is placed with a predetermined gap at a side of the tooth measuring apparatus with respect to the pair of pillar convex sections;
    observing a position of a regular reflection region of the tooth to be measured appearing in an image shot by the tooth measuring apparatus; and
    measuring by adjusting a relative angle between the tooth measuring apparatus and the tooth to be measured, while performing the observation.

6. The contact cap according to claim 1, wherein each of the pair of pillar convex sections is configured of an elastically distorted member.

7. The contact cap according to claim 1, wherein the contact cap is disposable.

8. The contact cap according to claim 1, wherein an inside of the cap section is shaped to be vertically and horizontally symmetrical so that the cap section is attachable to the tooth measuring apparatus even when upside down.

9. A contact cap for a dental tooth measuring apparatus comprising:
    a cap section which is attachable to cover a periphery of a shooting window section of the tooth measuring apparatus;
    an opening section which has a size to include a tooth to be measured and parts of a pair of adjacent teeth adjacent to the tooth to be measured, wherein the opening section is arranged before the cap section, and faces the shooting window section when the cap section is attached to the tooth measuring apparatus;
    a protrusion section which is placed below the opening section so as to protrude ahead of the tooth measuring apparatus, and which is biteable by the pair of adjacent teeth;
    a pair of pillar convex sections formed on an upper portion of the protrusion section for positioning tongue sides of the pair of adjacent teeth, wherein the pair of pillar convex sections are arranged separately from each other; and
    a wall section which is provided on the cap section and which is placed with a predetermined gap at a side of the tooth measuring apparatus with respect to the pair of pillar convex sections;
    a front upside section which forms an upside of the opening section; and
    at least one extending section which extends backward to one of left and right of the cap section, and which has a latch hole for latching to a latching protrusion of a top cover of the dental tooth measuring apparatus.

10. The contact cap according to claim 1, wherein the protrusion section further comprises:
    a concave section; and
    left and right upside sections rising from the concave section, wherein the pair of pillar convex sections are formed on the left and right upside sections.

11. The contact cap according to claim 10, wherein the pair of pillar convex sections formed on the left and right upside sections define first left and right upside sections of a front extending section, and second left and right upside sections.

12. The contact cap according to claim 1, wherein the size of the opening section is about 14 mm top to bottom and about 16 mm left to right.

13. The contact cap according to claim 1, wherein the wall section is placed at a position corresponding to a width of the protrusion section, the width of the protrusion section is 20 mm, and the wall section is placed substantially on a cylinder surface passing a position on an optical axis behind the pair of pillar convex sections by 5.1 mm.

14. A contact cap for a dental tooth measuring apparatus, comprising:
- a cap section which is attachable to cover a periphery of a shooting window section of the tooth measuring apparatus;
- an opening section which has a size to include a tooth to be measured and parts of a pair of adjacent teeth adjacent to the tooth to be measured, wherein the opening section is arranged before the cap section, and faces the shooting window section when the cap section is attached to the tooth measuring apparatus;
- a protrusion section which is placed below the opening section so as to protrude ahead of the tooth measuring apparatus and which is biteable by the pair of adjacent teeth;
- a pair of pillar convex sections formed on an upper portion of the protrusion section for positioning tongue sides of the pair of adjacent teeth, wherein the pair of pillar convex sections are arranged separately from each other; and
- a wall section which is provided on the cap section and which is placed with a predetermined gap at a side of the tooth measuring apparatus with respect to the pair of pillar convex sections,
- wherein the contact cap has a shape tapered from backward of the cap section toward the protrusion section.

15. A contact cap for a dental tooth measuring apparatus, comprising:
- a cap section which is attachable to cover a periphery of a shooting window section of the tooth measuring apparatus;
- an opening section which has a size to include a tooth to he measured and parts of a pair of adjacent teeth adjacent to the tooth to be measured, wherein the opening section is arranged before the cap section, and faces the shooting window section when the cap section is attached to the tooth measuring apparatus;
- a protrusion section which is placed below the opening section so as to protrude ahead of the tooth measuring apparatus and which is biteable by the pair of adjacent teeth;
- a pair of pillar convex sections formed on an upper portion of the protrusion section for positioning tongue sides of the pair of adjacent teeth, wherein the pair of pillar convex sections are arranged separately from each other; and
- a wall section which is provided on the cap section and which is placed with a predetermined gap at a side of the tooth measuring apparatus with respect to the pair of pillar convex sections,
- wherein the cap section has a shape tapered from backward to forward.

16. A contact cap for a dental tooth measuring apparatus, comprising:
- a cap section which is attachable to cover a periphery of a shooting window section of the tooth measuring apparatus;
- an opening section which has a size to include a tooth to be measured and parts of a pair of adjacent teeth adjacent to the tooth to be measured, wherein the opening section is arranged before the cap section, and faces the shooting window section when the cap section is attached to the tooth measuring apparatus;
- a protrusion section which is placed below the opening section so as to protrude ahead of the tooth measuring apparatus and which is biteable by the pair of adjacent teeth;
- a pair of pillar convex sections formed on an upper portion of the protrusion section for positioning tongue sides of the pair of adjacent teeth, wherein the pair of pillar convex sections are arranged separately from each other and face the opening section; and
- a wall section which is provided on the cap section and which is placed with a predetermined gap at a side of the tooth measuring apparatus with respect to the pair of pillar convex sections.

* * * * *